US007282205B2

(12) United States Patent
Schofield et al.

(10) Patent No.: US 7,282,205 B2
(45) Date of Patent: Oct. 16, 2007

(54) ANTI-HEPATITIS A VIRUS ANTIBODIES

(75) Inventors: Darren J. Schofield, Royston (GB); Suzanne U. Emerson, Gaithersburg, MD (US); Robert H. Purcell, Gaithersburg, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 156 days.

(21) Appl. No.: 10/494,676

(22) PCT Filed: Nov. 7, 2002

(86) PCT No.: PCT/US02/36077

§ 371 (c)(1),
(2), (4) Date: May 4, 2004

(87) PCT Pub. No.: WO03/040341

PCT Pub. Date: May 15, 2003

(65) Prior Publication Data

US 2004/0260067 A1 Dec. 23, 2004

Related U.S. Application Data

(60) Provisional application No. 60/339,109, filed on Nov. 7, 2001.

(51) Int. Cl.
*A61K 39/395* (2006.01)
*C07K 16/00* (2006.01)
*C12N 15/00* (2006.01)
*C12P 21/06* (2006.01)
*G01N 33/53* (2006.01)

(52) U.S. Cl. .............................. 424/141.1; 424/139.1; 530/388.1; 530/388.2; 530/388.3; 435/320.1; 435/69.1; 435/7.1

(58) Field of Classification Search .............. 530/387.3
See application file for complete search history.

(56) References Cited

U.S. PATENT DOCUMENTS

| 4,444,487 A | 4/1984 | Miller et al. |
| 4,614,793 A | 9/1986 | Hughes et al. |
| 4,745,055 A | 5/1988 | Schenk et al. |
| 4,777,245 A | 10/1988 | Foung et al. |
| 6,106,835 A | 8/2000 | Chang |

FOREIGN PATENT DOCUMENTS

| EP | 120694 | 10/1984 |
| EP | 125023 | 11/1984 |
| EP | 256654 | 2/1988 |
| WO | WO87/01131 | 2/1987 |
| WO | WO88/03565 | 5/1988 |
| WO | WO 01/40270 | 6/2001 |

OTHER PUBLICATIONS

Marks, JD et al "Human antibodies from V-gene libraries displayed on phage" J. Mol. Biol. vol. 222(1991) pp. 581-597.*
Macgregor, A. et al. "Monoclonal antibodies aginst hepatitis A virus" J. Clinical Microbiology, vol. 18(1983), No. 5, pp. 1237-1243.*
US-10-494-676-3.rpr: Alignments.*
Gane et al., "Clinical recurrence of hepatitis A following liver transplantation fro acute liver failure," *J. Medical Virol.* 45:35-39, 1995.
Schofield et al., "Identification by Phage Display and Characterization of Two Neutralizing Chimpanzee Monoclonal Antibodies to the Hepatitus E Virus Capsid Protein," *J. Virol.* 74(12):5548-5555, 2000.
Schofield et al., "Four Chimpanzee Monoclonal Antibodies Isolated by Phage Display Neutralize Hepatitus A Virus," *Virology* 292:127-136, 2002.
Van Meel et al., "Human and Chimpanzee Monoclonal Antibodies," *J. Immunol. Methods* 80:267-276, 1985.
Zesheng et al., "Selection of Human Anti-HAV McAb from a Phage Antibody Library," *Chinese J. Biotech.* 14(3):173-178, 1999.
Barbas, et al., "Assembly of Combinatorial Antibody Library on Phage Surfaces: the Gene III Site," *Proc. Natl. Acad. Sci U.S.A.* 88:7978-7982, 1991.
Ciocca, "Clinical Course and Consequences of Hepatitis A Infection," *Vaccine* 18 Suppl. 1, S71-74, 2000.
Falkner et al., "Expression of Mouse Immunoglobulin Genes in Monkey Cells," *Nature* 298:286-288, 1982.
Lefilliatre et al., "Fulminant Hepatitis A in Patients with Chronic Liver Disease," *Can. J. Public Health* 91(3), 168-170, 2000.
MacGregor et al., "Monoclonal Antibodies Against Hepatitis A Virus," *J. Clin. Microbiol.* 18(5): 1237-1243, 1983.
Marks et al., "By-passing immunization. Human antibodies from V-gene libraries displayed on Phage," *J. Mol. Biol.* 222:581-597, 1991.
Morrison, "Sequentially Derived Mutants of the Constant region of teh Heavy Chain of Murine Immunoglobulins," *J. Immunol.* 123(2):793-800, 1979.

(Continued)

*Primary Examiner*—Bruce R. Campell
*Assistant Examiner*—Bo Peng
(74) *Attorney, Agent, or Firm*—Klarquist Sparkman, LLP

(57) ABSTRACT

Chimpanzee monoclonal antibodies and antigen binding fragments including a γ1-chain CDR3 region that bind hepatitis A virus (HAV) antigen are disclosed herein. The antibodies neutralize HAV. Also disclosed are methods for using these antibodies and antigen binding fragments in the detection of hepatitis A virus, the inhibition of infection of a subject with hepatitis A virus, and in screening for agents that affect HAV.

24 Claims, 4 Drawing Sheets

OTHER PUBLICATIONS

Morrison et al., "Transfer and Expression of Immunoglobulin Genes," *Ann Rev. Immunol.* 2:239-256, 1984.

Nainan, Identification of Amino Acids Located in the Antibody Binding Sites of Human Hepatitus A Virus, *Virology* 191(2): 984-987, 1992.

O'Grady, "Fulminant hepatitus in patients with chronic liver disease," *J. Viral Hepat.* 7 Suppl. 1, 9-10, 2000.

Ping et al., "Identification of an immunodominant antigenic site involving the capsid protein VP3 of hepatitus A virus," *Proc. Natl. Acad. Sci. U.S.A.* 85(21):8281-8285, 1988.

Ping et al., "Antigenic Structure of Human Hepatitus A Virus Defined by Analysis of Escape Mutants Selected against Murine Monoclonal Antibodies," *J. Virol.* 66(4): 2208-2216, 1992.

Silberstein, et al., Neutralization of Hepatitus A Virus (HAV) by an Immunoadhesion Containing the Cysteine-Rich Region of HAV Cellular Receptor-1, *J. Virol.* 75(2): 717-725, 2001.

Stapleton et al., "Neutralization Escape Mutants Define a Dominant Immunogenic Neutralization Site on Hepatitis A Virus," *J. Virol.* 61(2): 491-498, 1987.

Tsarev et al., "Simian hepatitis A virus (HAV) strain AGM-27: comparison of genome structure and growth in cell culture with other HAV strains," *J. Gen. Virol.* 72(7): 1677-1683, 1991.

Uhlig et al., "Intertypic Cross-Neutralization of Polioviruses by Human Monoclonal Antibodies," *Virology* 163(1), 214-217, 1988.

Vento, "Fulminant hepatitis associated with hepatitis A virus superinfection in patients with chronic hepatitis C," *J. Viral Hepat.* 7 Suppl. 1, 7-8, 2000.

Watson et al., eds., Chapter 7 in *Recombinant DNA*, W. H. Freeman and Co., New York, pp. 99-133, 1992.

Williamson et al., "Human monoclonal antibodies against a plethora of viral pathogens from single combinatorial libraries," *Proc. Natl. Acad. Sci. U.S.A.* 90(9): 4141-4145, 1993.

Yang et al., CDR Walking Mutagenesis for the Affinity Maturation of a Potent Human Anti-HIV-1 Antibody into the Picomolar Range, *J. Mol. Biol.* 254(3): 392-403, 1995.

* cited by examiner

Figure 1

```
           FR1                              CDR1    FR2                    CDR2
HAV#4   EVQLLEQSGAEVKKPGASKVKSCKASGYRFS   NYAMH   WVRQAPGQSLEWMG   WINPVSGKTQFSQKFQG
HAV#5   .....R.......E.LTI..QG..DIFT       ..WIG   ....M..KG....    I..Y.RNSD.KY.PS...
HAV#6   ......PRLV..SQTLSLT.SV..ASLT       RGNYYWS .M..P..KG...I.   T.HSRGRPAYNTSLAS
HAV#14  ..........E.L.I...V..S.ST         ..WIA   ...M..KG....     I..S.SDST.KY.PA...

FR3                              CDR3                                FR4
HAV#4   RVTITRDTSASTVYNEVTSLTSEDTAVYYCTR   DLPGTWNFVDVFDI                    WGQGTMVTVSS
HAV#5   L...SA.K.TN.A.LQWN..GAS...I...V.   ASY.NY.YFYNM.V                    ..R..T..I..
HAV#6   ..AMSV.A.NNQFSLNLN.VTAA......A.    VFQSKGGA.WAPTTEWTYSYYYYMDV        ..R..T....
HAV#14  Q...SA.K.IN.A.LQWS...RAS...I...AK  STI.V.DYYYYM.V                    ..E..S..I..
```

Figure 3

SEQUENCE LISTING

```
<160> NUMBER OF SEQ ID NOS: 9

<210> SEQ ID NO 1
<211> LENGTH: 124
<212> TYPE: PRT
<213> ORGANISM: chimpanzee

<400> SEQUENCE: 1

Glu Val Gln Leu Leu Glu Gln Ser Gly Ala Glu Val Lys Lys Pro Gly
1               5                   10                  15

Ala Ser Val Lys Val Ser Cys Lys Ala Ser Gly Tyr Arg Phe Ser Asn
            20                  25                  30

Tyr Ala Met His Trp Val Arg Gln Ala Pro Gly Gln Ser Leu Glu Trp
        35                  40                  45

Met Gly Trp Ile Asn Pro Val Ser Gly Lys Thr Gln Phe Ser Gln Lys
    50                  55                  60

Phe Gln Gly Arg Val Thr Ile Thr Arg Asp Thr Ser Ala Ser Thr Val
65                  70                  75                  80

Tyr Met Glu Val Thr Ser Leu Thr Ser Glu Asp Thr Ala Val Tyr Tyr
                85                  90                  95

Cys Thr Arg Asp Leu Pro Gly Thr Trp Asn Phe Val Asp Val Phe Asp
            100                 105                 110

Ile Trp Gly Gln Gly Thr Met Val Thr Val Ser Ser
        115                 120

<210> SEQ ID NO 2
<211> LENGTH: 124
<212> TYPE: PRT
<213> ORGANISM: chimpanzee

<400> SEQUENCE: 2

Glu Val Gln Leu Leu Glu Gln Ser Gly Ala Glu Val Lys Lys Pro Gly
1               5                   10                  15

Glu Ser Leu Thr Ile Ser Cys Gln Gly Ser Gly Asp Ile Phe Thr Asn
            20                  25                  30

Tyr Trp Ile Gly Trp Val Arg Gln Met Pro Gly Lys Gly Leu Glu Trp
        35                  40                  45
```

```
Met Gly Ile Ile Tyr Pro Arg Asn Ser Asp Thr Lys Tyr Ser Pro Ser
        50                  55                  60

Phe Gln Gly Leu Val Thr Ile Ser Ala Asp Lys Ser Thr Asn Thr Ala
65                  70                  75                  80

Tyr Leu Gln Trp Asn Ser Leu Gly Ala Ser Asp Thr Ala Ile Tyr Tyr
                85                  90                  95

Cys Val Arg Ala Ser Tyr Gly Asn Tyr Asn Tyr Phe Tyr Asn Met Asp
                100                 105                 110

Val Trp Gly Arg Gly Thr Thr Val Thr Ile Ser Ser
            115                 120
```

<210> SEQ ID NO 3
<211> LENGTH: 137
<212> TYPE: PRT
<213> ORGANISM: chimpanzee

<400> SEQUENCE: 3

```
Glu Val Gln Leu Leu Glu Gln Ser Gly Pro Arg Leu Val Lys Pro Ser
1               5                   10                  15

Gln Thr Leu Ser Leu Thr Cys Ser Val Ser Gly Ala Ser Leu Thr Arg
                20                  25                  30

Gly Asn Tyr Tyr Trp Ser Trp Met Arg Gln Pro Pro Gly Lys Gly Leu
            35                  40                  45

Glu Trp Ile Gly Thr Ile His Ser Arg Gly Arg Pro Ala Tyr Asn Thr
        50                  55                  60

Ser Leu Ala Ser Arg Val Ala Met Ser Val Asp Ala Ser Asn Asn Gln
65                  70                  75                  80

Phe Ser Leu Asn Leu Asn Ser Val Thr Ala Ala Asp Thr Ala Val Tyr
                85                  90                  95

Tyr Cys Ala Arg Val Phe Gln Ser Lys Gly Gly Ala Val Trp Ala Pro
                100                 105                 110

Thr Thr Glu Trp Thr Tyr Ser Tyr Tyr Tyr Met Asp Val Trp Gly
            115                 120                 125

Arg Gly Thr Thr Val Thr Val Ser Ser
        130                 135
```

<210> SEQ ID NO 4
<211> LENGTH: 124
<212> TYPE: PRT
<213> ORGANISM: chimpanzee

<400> SEQUENCE: 4

```
Glu Val Gln Leu Leu Glu Gln Ser Gly Ala Glu Val Lys Lys Pro Gly
1               5                   10                  15

Glu Ser Leu Lys Ile Ser Cys Lys Val Ser Gly Ser Arg Ser Thr Asn
                20                  25                  30

Tyr Trp Ile Ala Trp Val Arg Gln Met Pro Gly Lys Gly Leu Glu Trp
            35                  40                  45

Met Gly Ile Ile Ser Pro Ser Asp Ser Thr Lys Tyr Ser Pro Ala
        50                  55                  60

Phe Gln Gly Gln Val Thr Ile Ser Ala Asp Lys Ser Ile Asn Thr Ala
65                  70                  75                  80

Tyr Leu Gln Trp Ser Ser Leu Arg Ala Ser Asp Thr Ala Ile Tyr Tyr
                85                  90                  95

Cys Ala Lys Ser Thr Ile Gly Val Trp Asp Tyr Tyr Tyr Met Asp
                100                 105                 110
```

```
Val Trp Gly Glu Gly Thr Ser Val Thr Ile Ser Ser
        115                 120
```

<210> SEQ ID NO 5
<211> LENGTH: 30
<212> TYPE: DNA
<213> ORGANISM: artificial sequence
<220> FEATURE:
<223> OTHER INFORMATION: primer

<400> SEQUENCE: 5

```
gcatgtacta gttgtgtcac aagatttggg                                         30
```

<210> SEQ ID NO 6
<211> LENGTH: 372
<212> TYPE: DNA
<213> ORGANISM: chimpanzee

<400> SEQUENCE: 6

```
gaggtgcagc tgctcgagca gtcagggggct gaggtgaaga agcctggggc ctcagtgaag        60
gtttcctgca aggcttctgg atacagattc agtaattatg ctatgcattg ggtgcgccag       120
gcccccggac aaagccttga gtggatgggg tggatcaacc ctgtcagtgg taagacacag       180
ttttcgcaga agttccaggg agagtcacc attaccaggg acacgtccgc gagcacagtc       240
tacatggagg tgaccagcct gacatctgag gacacggctg tatattattg tacgagagat       300
cttccgggca cctggaactt cgttgatgtc tttgatatat ggggccaagg gacaatggtc       360
accgtctctt ca                                                          372
```

<210> SEQ ID NO 7
<211> LENGTH: 372
<212> TYPE: DNA
<213> ORGANISM: chimpanzee

<400> SEQUENCE: 7

```
gaggtgcagc tgctcgagca gtctggggca gaggtgaaaa agcccgggga gtctctgacg        60
atctcctgtc agggctctgg agacatcttt accaactact ggatcggctg ggtgcgccag       120
atgcccggga aaggcctgga gtggatggga atcatctatc ctcgtaactc tgacaccaaa       180
tacagcccgt ccttccaagg cctggtcacc atctcagccg acaagtccac caacaccgcc       240
tacctgcagt ggaacagcct ggggggcctcg gacaccgcca tatattactg tgtaagagcg       300
tcctatggca actacaatta cttctacaac atggacgtct ggggcagagg gaccacggtc       360
accatctcct ca                                                          372
```

<210> SEQ ID NO 8
<211> LENGTH: 408
<212> TYPE: DNA
<213> ORGANISM: chimpanzee

<400> SEQUENCE: 8

```
gaggtgcagc tgctcgagtc gggcccacga ctggtgaagc cttcacagac cctgtccctt        60
acctgctctg tctctggtgc gtccctcact cgcggtaatt actactggag ttggatcgcc       120
cagccaccag ggaaaggact ggagtggatt gggaccattc attcccgtgg gaggcccgcc       180
tacaacacat ccctcgcgag tcgagtcgcc atgtcagtgg acgcgtccaa caaccaattc       240
tccctgaatc tcaactctgt caccgccgcg gacacggccg tgtattactg tgcgagagtt       300
ttccagtcga agggggggggc tgtctggggct ccaacaactg aatggacata ctcctattac       360
```

```
                                           -continued tactatatgg acgtctgggg cagagggacc acggtcaccg tctcctca              408

<210> SEQ ID NO 9
<211> LENGTH: 372
<212> TYPE: DNA
<213> ORGANISM: chimpanzee

<400> SEQUENCE: 9
gaggtgcagc tgctcgagca gtctggggca gaggtgaaaa agcccgggga gtctctaaag   60
atctcctgta aggtctctgg gtccaggtct accaactatt ggatcgcctg ggtgcgccag  120
atgcccggga aaggcctgga gtggatggga atcatctctc cttctgactc tactacgaaa  180
tacagcccgg ccttccaggg ccaggtcacc atctcagccg acaagtccat caacaccgcc  240
tacctgcagt ggagcagcct gcgggcctcg gacaccgcca tatattactg tgcgaaatcg  300
acaattgggg tgtgggacta ctactattac atggacgtct ggggcgaagg gacctcggtc  360
accatctcct ca                                                      372
```

ANTI-HEPATITIS A VIRUS ANTIBODIES

PRIORITY CLAIM

This is the § 371 U.S. National Stage of International Application No. PCT/US02/36077, filed Nov. 7, 2002, which was published in English under PCT Article 21(2), which in turn claims the benefit of U.S. Provisional Application No. 60/339,109, filed Nov. 7, 2001, which is incorporated by reference in its entirety herein.

FIELD

The present disclosure is related to the field of hepatitis virology, more specifically the disclosure is related to antibodies specific for hepatitis A virus (HAV) and the use of these antibodies in the diagnosis, treatment and prevention of hepatitis A.

BACKGROUND

Hepatitis A is an acute illness characterized by sudden onset of fever, malaise, nausea, anorexia, and abdominal discomfort, followed in several days by jaundice. Hepatitis A is the most common type of hepatitis reported in the United States, which reports an estimated 134,000 cases annually, and infects at least 1.4 million people worldwide each year (Source: *Cohn & Wolfe Healthcare*, Hepatitis Information Network website).

The causative agent of hepatitis A is the liver-infecting hepatitis A virus (HAV), which is a positive sense RNA virus that is transmitted via the fecal-oral route, mainly through contaminated water supplies and food sources. Hepatitis A virus is a member of the family Picornaviridae. HAV is thought to replicate in the oropharynx and epithelial lining of the intestines, where it initiates a transient viremia and subsequently infects the liver.

Humoral immunity has been shown to provide an effective defense against hepatitis A. Prior to the availability of the current inactivated virus vaccines, pooled human immune globulin preparations were routinely used to protect individuals traveling to areas of the world where hepatitis A is endemic (See Hollinger and Emerson, Hepatitis A Virus, 4th ed. In "*Fields Virology*" Vol. 1, 799–840, 2001). Unlike the neutralization of other members of the Picornaviridae, such as poliovirus and human rhinovirus, very little is understood about the mechanism of antibody-mediated neutralization of HAV. This is despite the fact that some strains of the virus grow in cell culture, albeit much less efficiently than do other picornaviruses.

The hepatitis A virion is an icosahedron comprised of pentamers of three structural proteins, VP1, VP2 and VP3. A fourth structural protein found in other picornaviruses, VP4, is truncated in HAV and has not been identified in virions. Epitopes recognized by the known murine neutralizing antibodies on the HAV capsid are dependent on the conformation of the antigen. Very few neutralizing antibodies have been generated to expressed antigens or subunit proteins.

Because antibodies elicited to HAV may neutralize the infectivity of the virus, the administration of a highly reactive, neutralizing anti-HAV antibody preparation to an individual who is at risk of infection, or who has recently been exposed to the infectious agent, would be of use in providing passive immunity to the immunized individual. Thus, there is a need for antibodies directed against HAV that may be used to protect individuals at risk for HAV infection or who have recently been exposed to HAV.

SUMMARY

The present disclosure relates to monoclonal antibodies and antigen binding fragments that specifically bind hepatitis A virus (HAV). The binding of HAV by the antibody or antigen binding fragment neutralizes HAV. The antibody can be a chimpanzee or a humanized antibody, such as but not limited to a humanized chimpanzee antibody.

In one embodiment of the disclosure, the antibodies or antigen binding fragments include amino acid sequences that encode the variable regions of the γ1 chain that determine the binding specificity.

Nucleic acids encoding the antibodies and antigen binding fragments are disclosed.

In several of the embodiments, methods are disclosed herein for the use of these antibodies or antigen binding fragments that specifically bind and neutralize HAV for prophylactic, therapeutic, and diagnostic agents for the inhibition for infection, treatment, and detection of hepatitis A in a subject. Methods are also disclosed to use these antibodies to screen for agents that affect HAV.

Pharmaceutical compositions including the HAV-binding antibodies and antigen binding fragments are disclosed.

Also disclosed herein are kits including a container with one or more of the antibodies or antigen binding fragments described herein, and, optionally, instructions for using the kits.

The foregoing and other features and advantages will become more apparent from the following detailed description of several embodiments, which proceeds with reference to the accompanying figures.

BRIEF DESCRIPTION OF THE FIGURES

FIG. 1 is an amino acid sequence alignment of the γ1 chain of the variable regions of the four chimpanzee MAbs HAV#4, HAV#5, HAV#6 and HAV#14.

FIG. 3 is a digital image showing the results of a virus-cell receptor blocking assay, with a range of dilutions of blocking Fabs HAV#4 (◆), HAV#5 (■), HAV#6 (▲) and HAV#14 (●), and a constant amount of soluble receptor HAVCR1.

SEQUENCE LISTING

Figure 2:
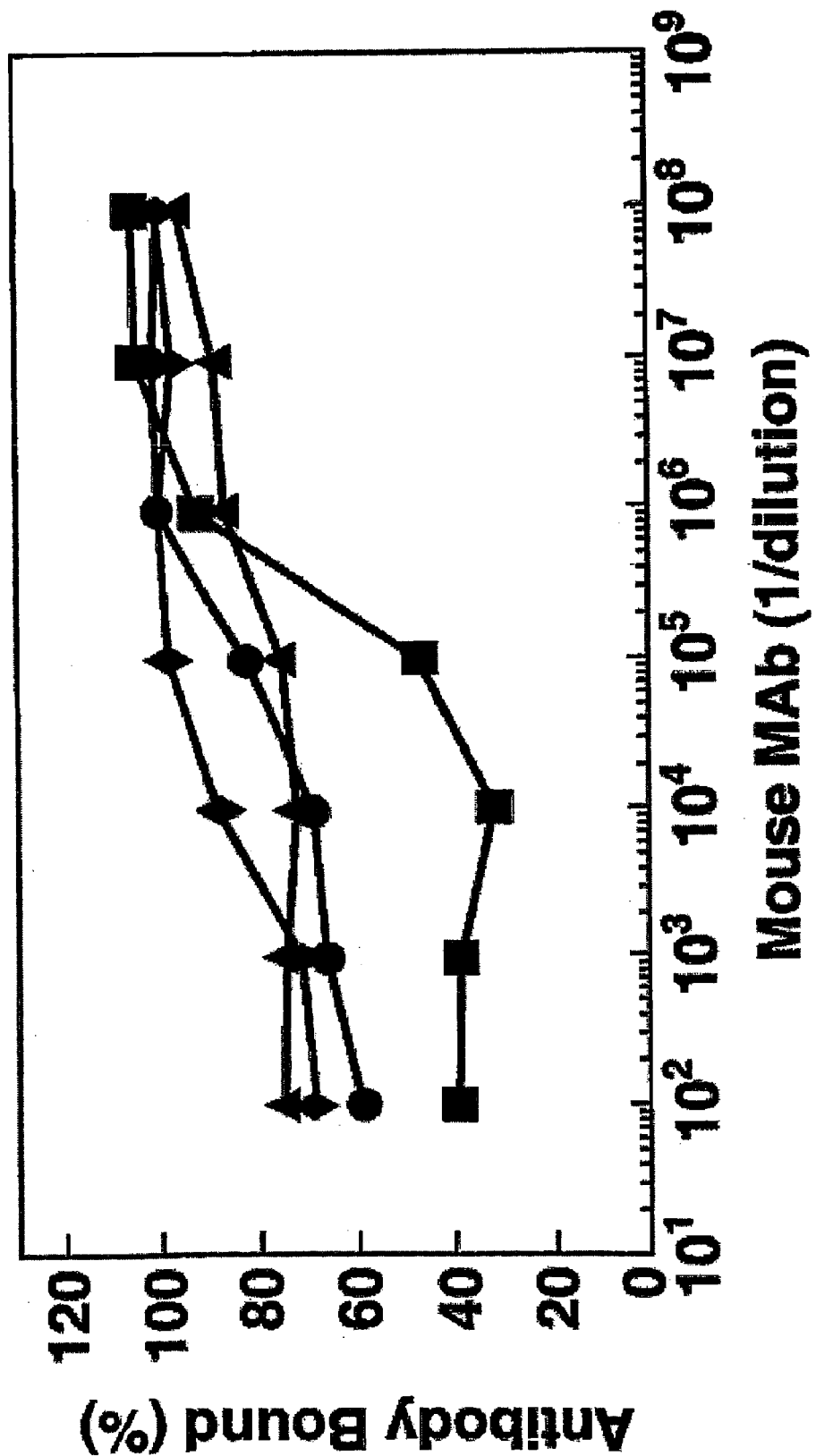
FIG. 2 is a digital image showing the results of an indirect competition assay between HAV#4 IgG, and the mouse MAbs, K3-2F2 (▲), K3-4C8 (■), K2-4F2 (●), and B5B3 (◆) (See MacGregor et al., *J. Clin. Microbiol.* 18(5): 1237–43, 1983).

The nucleic and amino acid sequences listed in the accompanying sequence listing are shown using standard letter abbreviations for nucleotide bases, and single letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the amino acid sequence of the γ1 chain of the variable region of HAV antibody number 4, ATCC deposit number PTA-3837, deposited Nov. 6, 2001.

SEQ ID NO: 2 shows the amino acid sequence of the γ1 chain of the variable region of HAV antibody number 5, ATCC deposit number PTA-3838, deposited Nov. 6, 2001.

SEQ ID NO: 3 shows the amino acid sequence of the γ1 chain of the variable region of HAV antibody number 6, ATCC deposit number PTA-3839, deposited Nov. 6, 2001.

SEQ ID NO: 4 shows the amino acid sequence of the γ1 chain of the variable region of HAV antibody number 14, ATCC deposit number PTA-3840, deposited Nov. 6, 2001.

SEQ ID NO: 5 shows a primer used in creation of a γ1/k antibody phage library.

SEQ ID NO: 6 shows the nucleic acid sequence encoding the γ1 chain of the variable region of HAV antibody number 4.

SEQ ID NO: 7 shows the nucleic acid sequence encoding the γ1 chain of the variable region of HAV antibody number 5.

SEQ ID NO: 8 shows the nucleic acid sequence encoding the γ1 chain of the variable region of HAV antibody number 6.

SEQ ID NO: 9 shows the nucleic acid sequence encoding the γ1 chain of the variable region of HAV antibody number 14.

The sequences encoding the γ1 chain of the variable region of HAV #4, #5, #6 and #14 have been deposited with EMBL/GenBank Data Libraries under Accession Nos. AF411913–AF411916, respectively, herein incorporated by reference.

DETAILED DESCRIPTION OF SEVERAL EMBODIMENTS

I. Abbreviations

| | |
|---|---|
| AST: | aspartate amino transferase |
| ALT: | alanine amino transferase |
| CDR: | complementarity-determining region |
| $CID_{50}$: | chimpanzee infectious dose 50 |
| DEAE: | diethyl aminoethyl |
| DNA: | deoxyribonucleic acid |
| ELISA: | enzyme-linked immunosorbant assay |
| FR: | framework region |
| GGTP: | gamma glutamyl transpeptidase |
| gpt: | guanine phosphoribosyltransferase |
| HAV: | hepatitis A virus |
| Ig: | immunoglobulin |
| IgG: | immunoglobulin G |
| kD: | kilodalton |
| MAb: | monoclonal antibody |
| neo: | neomycin |
| ORF: | open reading frame |
| RNA: | ribonucleic acid |
| TCR: | T-cell receptor |

II. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Abnormal: designates a deviation from normal characteristics. Normal characteristics can be found in a control, a standard for a population, etc. For instance, where the abnormal condition is a virus seropositive condition, sources of normal characteristics might include an individual who is not suffering from the disease, a population standard of individuals believed not to be suffering from the disease, etc.

Likewise, abnormal may refer to a condition that is associated with a disease. The term "associated with" includes an increased risk of developing the disease as well as the disease itself. For instance, a certain abnormality (such as an abnormality in liver function) can be described as being associated with the biological conditions of viral infection and tendency to develop decreased liver function.

Animal: a living multicellular vertebrate organism, a category that includes, for example, mammals and birds. A "mammal" includes both human and non-human mammals. Similarly, the term "subject" includes both human and veterinary subjects.

Antibody: immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody." Examples of binding fragments encompassed within the term antibody include (i) a Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., Nature 341:544–546, 1989) which consists of a VH domain; (v) an isolated complementarity determining region (CDR); and (vi) a F(ab')2 fragment, a bivalent fragment comprising two Fab fragments linked by a disulfide bridge at the hinge region.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol. 2:239, 1984).

Antigen: a molecule (e.g., polypeptide) that is specifically recognized and bound by an antibody. Those antigens that can induce antibody production are called immunogens.

Avidity: the overall strength of interaction between two molecules, such as an antigen and an antibody. Avidity depends on both the affinity and the valency of interactions. Therefore, the avidity of a pentameric IgM antibody, with ten antigen binding sites, for a multivalent antigen may be much greater than the avidity of a dimeric IgG molecule for the same antigen.

Biological samples: suitable biological samples include samples containing genomic DNA or RNA (including mRNA), obtained from body cells of a subject, such as those present in peripheral blood, urine, saliva, tissue biopsy, surgical specimen, amniocentesis samples, derivatives and fractions of blood such as serum, and liver biopsy material.

Capsid: a protein coat that covers the nucleoprotein core or nucleic acid of a virion. The capsid is built up of subunits (some integer multiple of 60, the number required to give strict icosahedral symmetry) that self assemble in a pattern typical of a particular virus. The subunits are often packed, in smaller capsids, into 5 or 6 membered rings (pentamers or hexamers) that constitute the morphological unit (capsomere). The packing of subunits is not perfectly symmetrical in most cases and some units may have strained interactions and are said to have quasi equivalence of bonding to adjacent units. The capsid proteins of HAV include VP1, VP2 and VP3, and may include VP4 (See Ping et al., *J. Virol.* 66(4): 2208–16, 1992).

Complementarity-determining region (CDR): the CDRs are three hypervariable regions within the VL or VH domain of an antibody molecule that form the N-terminal antigen-binding surface that is complementary to the three-dimensional structure of the bound antigen; the three hypervariable regions of the light chain form relative to each other in three-dimensional space. Proceeding from the N-terminus of a heavy or light chain, these complementarity-determining regions are denoted as "CDR1", "CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region. Alteration of a single amino acid within a CDR region can destroy the affinity of an antibody for a specific antigen (See Abbas et al., Cellular and Molecular Immunology, 4th ed. 143–5, 2000).

Conservative substitutions: modifications of a polypeptide that involve the substitution of one or more amino acids for amino acids having similar biochemical properties that do not result in change or loss of a biological or biochemical function of the polypeptide. These "conservative substitutions" are likely to have minimal impact on the activity of the resultant protein. In one embodiment, a conservative substitution of a CDR region does not change the antigen binding of the CDR. Table 1 shows non-limiting examples of amino acids that may be substituted for an original amino acid in a protein, and which are regarded as conservative substitutions.

TABLE 1

| Original Residue | Conservative Substitutions |
|---|---|
| ala | ser |
| arg | lys |
| asn | gln; his |
| asp | glu |
| cys | ser |
| gln | asn |
| glu | asp |
| gly | pro |
| his | asn; gln |
| ile | leu; val |
| leu | ile; val |
| lys | arg; gln; glu |
| met | leu; ile |
| phe | met; leu; tyr |
| ser | thr |

TABLE 1-continued

| Original Residue | Conservative Substitutions |
|---|---|
| thr | ser |
| trp | tyr |
| tyr | trp; phe |
| val | ile; leu |

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. A cDNA sequence variant may, for example, introduce no more than twenty, and for example fewer than ten amino acid substitutions into the encoded polypeptide. Variant amino acid sequences may, for example, be 80, 90 or even 95% or 98% identical to the native amino acid sequence. Programs and algorithms for determining percentage identity can be found at the NCBI website.

Control: substance used during a screening or detection assay to aid in gauging the result. For instance, in an assay screening for or detecting HAV, a control might be a sample taken from a subject known to have active HAV infection or a subject known to be free of HAV infection. A control can also be a sample containing a known amount of HAV virions, or a standard curve. A control can be used to gauge the success of the assay itself, and/or to prevent detection of false positives or false negatives in a sample.

DNA: deoxyribonucleic acid. DNA is a long chain polymer that comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Encode: a polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Epitope: the site on an antigen recognized by an antibody as determined by the specificity of the amino acid sequence.

Fab fragment (fragment with specific antigen binding): Fab fragments are the products of antibody molecule obtained by cleavage with an enzyme that leaves the antigen binding (variable) portion intact, but removes the constant domain. The Fab fragment consists of the light chain and the N-terminal half of the heavy chain held together by an interchain disulfide bond. Fab fragments include FAbs, Fvs, and single-chain Fvs (scFvs). These antibody fragments are defined as follows: (1) FAb, the fragment that contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) (FAb')2, the fragment of the antibody obtained by treating whole antibody with the enzyme pepsin without subsequent reduction; (4) F(Ab')2, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Framework region (FR): the framework regions are conserved sequences flanking the three highly divergent complementarity-determining regions (CDRs) within the variable regions of the heavy and light chains of an antibody. Some FR residues may contact bound antigen; however, FRs are primarily responsible for folding the variable region into the antigen-binding site, particularly the FR residues directly adjacent to the CDRs.

Functional fragments and variants of a polypeptide: includes those fragments and variants that maintain one or more functions of the parent polypeptide, such as the binding of the antibodies or antigen binding fragments of the antibodies to HAV. A functional fragment or variant is defined herein as an antibody or antigen binding fragment that specifically binds to an epitope of hepatitis A virus (HAV). It includes any polypeptide 8 or more, or 10 or more, or 15 or more, or 20 or more, or 25 or more amino acid residues in length that is capable of binding HAV. It is recognized that the gene or cDNA encoding a polypeptide can be considerably mutated without materially altering one or more of the polypeptide's functions. The genetic code is well known to be degenerate, and thus degenerate variants use different codons to encode the same amino acids. A conservative variant is a polypeptide in which an amino acid substitution is introduced, but the mutation can be conservative and have no material impact on the essential functions of a protein (See Stryer, Biochemistry 3rd Ed., 1988). In addition, part of a polypeptide chain can be deleted without impairing or eliminating all of its functions. Insertions or additions can also be made in the polypeptide chain, for example, adding epitope tags—without impairing or eliminating its functions (Ausubel et al., *J. Immunol.* 159(4): 1669–75, 1997. Thus, an antibody or antigen binding fragment of the disclosure could be modified by adding or deleting portions of the amino acid sequences disclosed herein, or by using conservative substitutions of the sequences, yet retain the ability to bind to and neutralize HAV. In addition, a fragment can be derivatized to improve the biochemical stability of the fragment. One specific, non-limiting example of a derivatized antibody or antigen binding fragment is conjugation of the antibody or fragment to a conjugate including a polymeric backbone, such as polyethylene glycol ("PEG"), cellulose, dextran, agarose, or an amino acid copolymer (See U.S. Pat. No. 6,106,835). Such modifications are within the scope of the disclosure.

Other modifications that can be made without materially impairing one or more functions of a polypeptide include, for example, in vivo or in vitro chemical and biochemical modifications or that incorporate unusual amino acids. Such modifications include, for example, acetylation, carboxylation, phosphorylation, glycosylation, ubiquination, labeling, e.g., with radionuclides, and various enzymatic modifications, as will be readily appreciated by those well skilled in the art. These modifications that do not alter the ability of the antibodies or antigen binding fragments of the antibodies to bind to and neutralize HAV are within the scope of the disclosure. A variety of methods for labeling polypeptides and of substituents or labels useful for such purposes are well known in the art, and include radioactive isotopes such as 32P, fluorophores, chemiluminescent agents, and enzymes.

Hepatitis: is a disorder in which viruses or other mechanisms (e.g., autoimmune or toxic mechanisms) produce inflammation in liver cells, resulting in their injury or destruction. In most cases this inflammatory process is triggered when the immune system fights off infections caused by viruses. Inflammation of the liver can also occur from medical problems, drugs, alcoholism, chemicals, and environmental toxins. Hepatitis varies in severity from a self-limited condition with total recovery to a life-threatening or life-long disease. Hepatitis manifests as either short-term (acute hepatitis) or prolonged (chronic hepatitis). In some cases, acute hepatitis develops into a chronic condition, but chronic hepatitis can also occur on its own. Although chronic hepatitis is generally the more serious condition, patients having either condition can experience varying degrees of severity. The chronic forms of hepatitis persist for prolonged periods (See Cecil Textbook of Medicine, 19th ed. Wyngaarden, Smith and Bennett eds., W. B. Saunders Co., 1992; WebMD website).

Most cases of hepatitis are caused by viruses that attack the liver. Five hepatitis viruses are known, called hepatitis A virus (HAV), hepatitis B virus (HBV), hepatitis C virus (HCV), hepatitis D virus (HDV), and hepatitis E virus (HEV). HBV is composed of DNA while HAV, HCV, HDV, and HEV are RNA viruses. The viruses for hepatitis are found in semen, blood, and saliva and are usually spread by blood transfusions, contaminated needles, contaminated food and water sources, and exposure to contaminated fecal matter or sexual contact with an infected individual. Hepatitis A virus can be detected in a biological sample using an antibody that exhibits specific binding to the virus capsid.

Hepatitis A is an illness characterized by sudden onset of fever, malaise, nausea, anorexia, and abdominal discomfort, followed in several days by jaundice. The causative agent of hepatitis A is the hepatitis A virus (HAV), a positive sense RNA virus that is a member of the family Picornaviridae. HAV is transmitted via the fecal-oral route, mainly through contaminated water supplies and food sources. HAV has a single molecule of RNA surrounded by a small (27 nm diameter) protein capsid and a buoyant density in CsCl of 1.33 g/ml. The genome is approximately 7.5 kb in length. One method of diagnosing Hepatitis A is detection of IgM-class anti-HAV in serum collected during the acute or early convalescent phase of disease. Humoral immunity provides an effective defense against hepatitis A.

Idiotope: a unique determinant on an antibody or TCR molecule, usually formed by one or more of the hypervariable regions. Idiotopes may be recognized as "foreign" in an individual because they are usually present in quantities too low to induce self-tolerance.

Idiotype: the property of a group of antibodies or T cell receptors defined by their sharing a particular idiotype; i.e., antibodies that share a particular idiotope belong to the same idiotype. "Idiotype" may be used to describe the collection of idiotopes expressed by an Ig molecule. An "anti-idiotype" antibody may be prepared to a monoclonal antibody by methods known to those of skill in the art and may be used to prepare pharmaceutical compositions rather than using monoclonal antibodies.

Immune complex: the binding of antibody to a soluble antigen forms an immune complex. The formation of an immune complex in vitro can be detected through conventional methods, for instance immunohistochemistry, immunoprecipitation, flow cytometry, immunofluorescence microscopy, ELISA, immunoblotting ("western"), and affinity chromatography. Additionally, the terms "immunological binding affinity" and "immunoreactive" as used interchangeably herein, refer to the non-covalent interactions of the type that occur between an immunoglobulin molecule that specifically binds an antigen. The affinity of immunological binding interactions may be expressed in terms of the dissociation constant (Kd) of the interaction, wherein a smaller Kd represents a greater affinity. Immunological binding properties of selected antibodies may be quantified using methods well known in the art. One such method entails measuring the rates of antigen-binding site/antigen complex association and dissociation, wherein those rates depend on the concentrations of the complex partners, the affinity of the interaction, and geometric parameters that equally influence the rate in both directions. (See, Davies et al., *Ann. Rev. Biochem.*, 59:439–73, 1990).

Immunoprophylaxis: the use of vaccines or antibody-containing preparations to provide immune protection against a specific disease. "Passive immunoprophylaxis" involves the administration of antibodies formed in another host to a subject to provide disease-specific immune protection. (See Marzan et al., *J. Hepatol.* 34(6):903–910, 2001).

Isolated: an "isolated" biological component (such as a nucleic acid molecule, protein or organelle) has been substantially separated or purified away from other biological components in the cell of the organism in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: a detectable compound or composition that is conjugated directly or indirectly to another molecule to facilitate detection of that molecule. Specific, non-limiting examples of labels include fluorescent tags, enzymatic linkages, and radioactive isotopes.

Monoclonal antibody: an antibody produced by a single clone of B-lymphocytes. Monoclonal antibodies are produced by methods known to those of skill in the art, for instance by making hybrid antibody-forming cells from a fusion of myeloma cells with immune spleen cells.

Neutralize: an antibody that can inhibit the infectivity of a virus or toxicity of a toxin molecule is said to "neutralize" the virus or toxin. Such antibodies are known as "neutralizing antibodies" and the process of inactivation is termed "neutralization."

Nucleotide: "nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: an oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10–25 bases, such as 12, 15 or 20 bases.

Operably linked: a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame (ORF): a series of nucleotide triplets (codons) coding for amino acids without any internal termination codons. These sequences are usually translatable into a peptide.

Panning: a technique used to select phage that contain antibodies with binding specificity to an antigen of interest. In one non-limiting example, a phage library containing various cloned antibodies is produced and grown in a suitable medium from which phage may be purified. The grown phage library is then added to a medium that contains immobilized antigen of interest. Phages that specifically bind the antigen of interest are eluted by any known method (e.g., pH shock) and unbound phages are removed by washing. The isolated phage are then produced in bulk, for instance by infection of bacteria and growth of colonies on plates. Colonies may then be grown in a suitable medium. In one embodiment, multiple rounds of panning are performed to produce isolated phage specific to an antigen(s) of interest.

Phage display: a technique wherein DNA sequences are amplified and cloned into phage to create a "phage library," in which the phage present on their surface the proteins encoded by the DNA. In one embodiment, a phage library is produced that expresses immunoglobulins to HAV, HBV, HCV, HDV and HEV. Antigen specific immunoglobulins can then be selected for expression and purification. Individual phage are rescued through interaction of the displayed protein with a ligand, and the specific phage is amplified by infection of bacteria.

Pharmaceutical agent: a chemical compound, polypeptide, peptidomimetic or other composition, including antibodies or antigen binding fragments that are capable of inducing a desired therapeutic or prophylactic effect when properly administered to a subject or a cell. "Incubating" includes a sufficient amount of time for an agent to interact with a cell. "Contacting" includes incubating the agent in solid or in liquid form with a cell. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

A "therapeutically effective amount" is a quantity of a chemical composition or an anti-viral agent sufficient to achieve a desired therapeutic or prophylactic effect in a subject being treated. For instance, this can be the amount necessary to inhibit viral replication or to measurably alter outward symptoms of the viral infection, such as sudden onset of fever, malaise, nausea, anorexia, and abdominal discomfort in the case of an HAV infection. In one embodiment, this amount is sufficient to measurably inhibit (e.g., neutralize) virus replication or infectivity. In another embodiment, the amount is sufficient to prevent an infection in an individual at risk of an HAV infection. When administered to a subject, a dosage will generally be used that will achieve target tissue concentrations (for example, in liver cells) that has been shown to achieve in vitro inhibition of viral replication.

Pharmaceutically acceptable carriers: the pharmaceutically acceptable carriers useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of the proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Picornaviruses: are RNA viruses wherein the viral genome is infectious RNA. Picornaviruses include aphthovirus, cardiovirus, hepatovirus (of which hepatitis A virus is a species), enterovirus and rhinovirus. The 5' UTR contains a "clover-leaf" secondary structure known as the IRES: Internal Ribosome Entry Site, where translation is initiated. The IRES allows picornavirus RNAs to continue to be translated after degradation of the cap-binding complex typically involved in translation initiation. Replication occurs in the cytoplasm, and can occur even in enucleated cells, and typically lasts between 5–10 hours.

Polypeptide: refers to a polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "fragment" refers to a portion of a polypeptide that is at least 8, 10, 15, 20 or 25 amino acids in length. The term "functional fragments of a polypeptide" refers to all fragments of a polypeptide that retain an activity of the polypeptide (e.g., the binding of an antigen). Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

Primers: nucleic acid primers can be readily prepared based on a nucleic acid sequence. Primers are short nucleic acid molecules, preferably DNA oligonucleotides 10 nucleotides or more in length. In some embodiments, longer DNA oligonucleotides can be about 15, 17, 20, or 23 nucleotides or more in length. Primers can be annealed to a complementary target nucleic acid (DNA or RNA) by nucleic acid hybridization to form a hybrid between the primer and the target nucleic acid, and then the primer extended along the target nucleic acid by a DNA polymerase enzyme. Primer pairs can be used for amplification of a nucleic acid sequence, e.g., by the polymerase chain reaction (PCR) or other nucleic-acid amplification methods known in the art.

Methods for preparing and using primers are described, for example, in Sambrook, Fritsch, and Maniatis, Molecular Cloning: a Laboratory Manual, 2nd Edition, Cold Spring Harbor Laboratory Press, USA, (1989); Ausubel et al. (In Current Protocols in Molecular Biology, Greene Publ. Assoc. and Wiley-Intersciences, 1998), and Innis et al. (PCR Protocols, A Guide to Methods and Applications, Academic Press, Inc., San Diego, Calif., 1990). PCR primer pairs can be derived from a known sequence, for example, by using computer programs intended for that purpose such as Primer (Version 0.5, © 1991), Whitehead Institute for Biomedical Research, Cambridge, Mass.). One of ordinary skill in the art will appreciate that the specificity of a particular primer increases with its length. Thus, for example, a primer comprising 30 consecutive nucleotides will anneal to a target sequence with a higher specificity than a corresponding primer of only 15 nucleotides. Thus, in order to obtain greater specificity, primers can be selected that comprise at least 17, 20, 23, 25, 30, 35, 40, 45, 50 or more consecutive nucleotides.

Probes: a probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., Sambrook et al. (In Molecular Cloning: A Laboratory Manual, CSHL, New York, 1989) and Ausubel et al. (In Current Protocols in Molecular Biology, John Wiley & Sons, New York, 1998).

Protein: a biological molecule expressed by a gene and comprised of amino acids.

Purified: the term "purified" does not require absolute purity; rather, it is intended as a relative term. Thus, for example, a purified protein preparation is one in which the protein referred to is more pure than the protein in its natural environment within a cell or within a production reaction chamber (as appropriate). Likewise, a purified organelle preparation is one in which the specified antibody is more pure than in its natural environment, so that only relatively insubstantial amounts (e.g., less than 10% relative) of other antibodies (or markers for other organelles) are present in the preparation.

Recombinant: a recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Radioimmunofocus assay (RIFA): a technique used to detect the presence of antigen-antibody binding using the measurement of radioactivity as the method of detection. Such techniques are well known in the art (See Raychaudhuri et al., *J. Virol.* 72(9): 7467–76, 1998).

RNA: ribonucleic acid. RNA is a polymer formed from covalently linked ribonucleotide monomers. The repeating units in RNA polymers are four different nucleotides, each of which comprises one of the four bases, adenine, guanine, cytosine and uracil bound to a ribose sugar to which a phosphate group is attached.

Sequence identity: the similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of the HAV antibodies or antigen binding fragments, and the corresponding cDNA sequence, will possess a relatively high degree of sequence identity when aligned using standard methods. This homology will be more significant when the orthologous proteins or cDNAs are derived from species that are more closely related (e.g., human and chimpanzee sequences), compared to species more distantly related (e.g., human and murine sequences).

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48: 443 (1970); Pearson and Lipman, *Proc. Natl. Acad. Sci. USA* 85: 2444 (1988); Higgins. and Sharp, *Gene,* 73: 237–244 91988); Higgins and Sharp, *CABIOS* 5:151–153, 1989; Corpet et al., *Nuc. Acids Res.* 16, 10881–90, 1988; Huang et al., *Computer Appls. in the Biosciences* 8, 155–65, 1992; and Pearson et al., *Meth. Mol. Bio.* 24, 307–31 (1994). Altschul et al., *J. Mol. Biol.* 215:403–410 (1990), presents a detailed consideration of sequence alignment methods and homology calculations.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence remains hybridized to a perfectly matched probe or complementary strand. Conditions for nucleic acid hybridization and calculation of stringencies can be found in Sambrook et al. (1989) Molecular Cloning: A Laboratory Manual, CSHL, New York and Tijssen (1993) Laboratory Techniques in Biochemistry and Molecular Biology—Hybridization with Nucleic Acid Probes Part I, Chapter 2, Elsevier, N.Y. Nucleic acid molecules that hybridize under stringent conditions to a given HAV sequence will typically hybridize under wash conditions of 2×SSC at 50° C.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: an agent that binds substantially only to a defined target. Thus an antibody or antibody fragment-specific binding agent binds substantially only the defined antibody or antibody fragment, or an antibody region within a protein, such as a fusion protein. As used herein, the term "HAV specific binding agent," where HAV refers to a specific protein or peptide of HAV, includes anti-HAV antibodies (and functional antibody fragments thereof) and other agents (such as potential therapeutic agents) that bind substantially only to HAV.

Antibodies may be produced using standard molecular procedures described in a number of texts, including Harlow and Lane (Antibodies, A Laboratory Manual, CSHL, New York, 1988). The determination that a particular agent binds substantially only to the target protein or peptide may readily be made by using or adapting routine procedures. One suitable in vitro assay makes use of the Western blotting procedure (described in many standard texts, including Harlow and Lane, Antibodies, A Laboratory Manual, CSHL, New York, 1988). Western blotting may be used to determine that a given protein binding agent, such as an anti-HAV protein monoclonal antibody, binds substantially only to the specified HAV protein.

Shorter fragments of antibodies can also serve as specific binding agents. For instance, FAbs, Fvs, and single-chain Fvs (scFvs) that bind to a protein or peptide HAV would be HAV-specific binding agents.

Subject: living multi-cellular vertebrate organisms, a category that includes both human and non-human mammals.

T-Cell Receptor (TCR): is a disulfide-linked heterodimer of the highly variable α and β chains expressed on T cells as a complex with the invariant CD3 chains.

Treatment: refers to both prophylactic inhibition of initial infection, and therapeutic interventions to alter the natural course of an untreated disease process, such as infection with a virus (e.g., HAV infection).

Transfected: a transfected cell is a cell into which a nucleic acid molecule has been introduced by molecular biology techniques. As used herein, the term "transfection" encompasses all techniques by which a nucleic acid molecule might be introduced into such a cell, including transfection with viral vectors, transformation with plasmid vectors, and introduction of DNA by electroporation, lipofection, and particle gun acceleration.

Variable region (also variable domain or V domain): the regions of both the light-chain and the heavy-chain on an immunoglobulin that contain antigen-binding sites. The regions are composed of polypeptide chains containing four relatively invariant "framework regions" (FRs) and three highly variant "hypervariable regions" (HVs). Because the HVs constitute the binding site for antigen(s) and determine specificity by forming a surface complementarity to the antigen, they are more commonly termed the "complementarity-determining regions", or CDRs, and are denoted CDR1, CDR2, and CDR3. Because both of the CDRs from the heavy- and light-chain domains contribute to the antigen-binding site, it is the three-dimensional combination of the heavy and the light chain that determines the final antigen specificity.

Within the heavy- and light-chain, the framework regions surround the CDRs. Proceeding from the N-terminus of a heavy or light chain, the order of regions is: FR1-CDR1-FR2-CDR2-FR3-CDR3-FR4. As used herein, the term "variable region" is intended to encompass a complete set of four framework regions and three complementarity-determining regions. Thus, a sequence encoding a "variable region" would provide the sequence a complete set of four framework regions and three complementarity-determining regions.

Vector: a nucleic acid molecule as introduced into a host cell, thereby producing a transformed host cell. Recombinant vectors are vectors having recombinant nucleic acid sequences. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. "Comprise" means "include." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

III. Monoclonal Antibodies

A. Proteins and Their Expression

Disclosed herein are monoclonal antibodies or antigen binding fragments that specifically bind hepatitis A virus. In one embodiment, the specific binding of the monoclonal antibody neutralizes hepatitis A virus. See Schofield et al., *Virology* 292(1):127–136, 2002. In one embodiment, the monoclonal antibody is an IgG molecule. The monoclonal antibodies each have a unique CDR3 region within the variable region. In one embodiment the CDR3 region of the γ1 heavy chain has a sequence as set forth in amino acids 100–113 of SEQ ID NO: 1, amino acids 100–113 of SEQ ID NO: 2, amino acids 101–126 of SEQ ID NO: 3, or amino acids 100–113 of SEQ ID NO: 4. Nucleic acid sequences encoding these amino acids, conservative variants of the amino acids, and variants due to the degeneracy of the genetic code are also provided herein.

The CDR1 region of the variable region of a monoclonal antibody that binds HAV can have a sequence as set forth in amino acids 32–36 of SEQ ID NO: 1, amino acids 32–36 of SEQ ID NO: 2, amino acids 32–38 of SEQ ID NO: 3, or amino acids 32–36 of SEQ ID NO: 4. Any of the disclosed CDR3 regions can be combined with any of the disclosed CDR1 regions within the antibody variable region. In one specific, non-limiting example, the variable region includes amino acids 100–113 of SEQ ID NO: 1 and amino acids 32–36 of SEQ ID NO: 2. In another specific, non-limiting example, the variable region includes amino acids 101–126 of SEQ ID NO: 3 and amino acids 32–38 of SEQ ID NO: 3.

The CDR2 region of the variable region of a monoclonal antibody that binds HAV can have a sequence as set forth in amino acids 51–67 of SEQ ID NO: 1, amino acids 51–67 of SEQ ID NO: 2, amino acids 53–68 of SEQ ID NO: 3, or amino acids 51–67 of SEQ ID NO: 4. Any of the disclosed CDR3 regions can be combined with any of the CDR1 regions, and with any of the disclosed CDR2 regions within an antibody variable region. Thus, in one specific, non-limiting example, the variable region includes amino acids 100–113 of SEQ ID NO: 1, amino acids 32–36 of SEQ ID NO: 2 and amino acids 53–68 of SEQ ID NO: 3. In another specific, non-limiting example, the variable region includes amino acids 100–113 of SEQ ID NO: 2, amino acids 32–36 of SEQ ID NO: 2 and amino acids 51–67 of SEQ ID NO: 2.

The disclosure further includes the amino acid sequences that encode the framework regions of the variable region of antibodies that bind HAV and conservative variants thereof. These sequences are provided in amino acids 1–31, 37–50, 68–99, and 114–124 of SEQ ID NO: 1, amino acids 1–31, 37–50, 68–99, and 114–124 of SEQ ID NO: 2, amino acids 1–31, 39–52, 60–100, and 127–137 of SEQ ID NO: 3, and amino acids 1–31, 37–50, 68–99, and 114–124 of SEQ ID NO: 4.

In one specific, non-limiting example, the variable region of a monoclonal antibody that binds HAV includes the amino acid sequence as set forth in SEQ ID NO: 1, SEQ ID NO: 2, SEQ ID NO: 3, or SEQ ID NO: 4.

In another specific, non-limiting example, the monoclonal antibody that binds HAV is a chimpanzee antibody. Alternatively, the monoclonal antibody that binds HAV antibody is a humanized antibody, such as but not limited to a humanized chimpanzee antibody. In yet another specific non-limiting example, the monoclonal antibody is a monoclonal antibody that has been subjected to affinity maturation. One of skill in the art can readily perform affinity maturation (see, for example, Yang et al., *J. Mol. Biol.* 254(3): 392–403, 1995).

The disclosed antibodies or antigen binding fragments bind to the capsid protein of HAV. In one embodiment, the specific binding of antibodies or antigen binding fragments to HAV neutralizes the virus. There are several in vitro assays known in the art that may be used to assess the capacity of a given antibody to neutralize a virus. One specific, non-limiting example of an assay measures the neutralization of known strains of hepatitis A, such as HM-175 and AGM-27, by the monoclonal antibodies of the present disclosure is an example of neutralizing activity in vitro (e.g., see Table 3). Another specific, non-limiting example of an assay measures the neutralization of a recombinant, laboratory-created strain of hepatitis A (e.g., VP3-070, see Table 3).

B. Nucleic Acids and Their Expression

The polypeptides disclosed herein can be made using techniques known to one of skill in the art (e.g. see WO 97/47732, herein incorporated by reference in its entirety). Briefly, each chain of the polypeptide is constructed or selected. In one embodiment, the polypeptides disclosed herein are produced using recombinant technology. Variants of the nucleic acids include variations due the degeneracy of the genetic code. Further, the polynucleotide sequences may be modified by adding tags that can be readily quantified, where desirable. Probes or primers can be used to assay the presence of the nucleic acid sequences in the host cell, or selectable markers can be included to facilitate detection of the nucleic acid sequences in a host cell.

The antibodies or antigen binding fragments of the antibodies can be modified by conventional techniques for inclusion in a library, for instance a recombinant cDNA library. Such a library can be used to store the antibodies or antigen binding fragments of the antibodies and serve as a convenient source from which the antibodies or antigen binding fragments may be produced for later use by techniques known to those of skill in the art (See Watson et al., Recombinant DNA, 102-04, 1992).

Methods and plasmid vectors for producing proteins in bacteria are described in Sambrook et al. (In: Molecular Cloning: A Laboratory Manual, Ch. 17, CSHL, New York, 1989), and Ausubel et al. (Short Protocols in Molecular Biology, 4th edition, Chapter 16, Wiley, New York, 1999). Such fusion proteins can be made in large amounts, are easy to purify, and can be used in immunogenic assays. Native proteins can be produced in bacteria by placing a strong, regulated promoter and an efficient ribosome-binding site upstream of the cloned gene. If low levels of protein are produced, additional steps can be taken to increase protein production; if high levels of protein are produced, purification is relatively straightforward. Suitable methods are presented in Sambrook et al. (In Molecular Cloning: A Laboratory Manual, CSHL, New York, 1989) and are well known in the art. Often, proteins expressed at high levels are found in insoluble inclusion bodies. Methods for extracting proteins from these aggregates are described by Sambrook et al. (In Molecular Cloning: A Laboratory Manual, Ch. 17, CSHL, New York, 1989) and Ausubel et al. (Short Protocols in Molecular Biology, 4th edition, Chapter 16, Wiley, New York, 1999). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). The monoclonal antibodies that bind to HAV can be isolated, purified and lyophilized.

The nucleic acid sequence encoding the protein can also be inserted into other cloning vehicles, such as other plasmids, bacteriophages, cosmids, animal viruses and yeast artificial chromosomes (YACs) (Burke et al., *Science* 236: 806-821, 1987). A suitable expression system can be chosen to express the nucleic acid sequences in a eurkaryotic system. Numerous types of appropriate expression vectors and host cell systems are known in the art, including but not limited to systems for expression in mammalian and yeast cells. Suitable host cells or cell lines for transfection include human 293 cells, chinese hamster ovary cells (CHO), murine L cells, monkey cells (e.g. COS-1 or COS-7), or murine 3T3 cells (e.g., see U.S. Pat. No. 4,419,449, or Gething and Sambrook, *Nature* 293:620, 1981.

For expression in mammalian cells, the nucleic acid sequence encoding the monoclonal antibodies that bind HAV can be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct can be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The nucleic acid sequence can be introduced into eukaryotic expression vectors by conventional techniques. These vectors are designed to permit the transcription of the nucleic acid in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, A Manual of Methods for Baculovirus Vectors and Insect Cell Culture Procedures, Texas Agricultural Experiment Station Bulletin No. 1555, 1987; Ausubel et al., Chapter 16 in Short Protocols in Molecular Biology, 1999) or by using vectors that contain promoters amenable to modulation, for example, the glucocorticoid-responsive promoter from the mouse mammary tumor virus (Lee et al., *Nature* 294:228, 1982).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines may be used to produce monoclonal antibodies that bind HAV on a continuous basis. One can also produce cell lines that have amplified the number of copies of the vector (and therefore of the cDNA as well) to create cell lines that can produce high levels of the gene product (Alt et al., *J. Bio. Chem.* 253:1357, 1978).

The transfer of DNA into eukaryotic, in particular human or other mammalian cells, is now a conventional technique. Thus, in one specific, non-limiting embodiment, the nucleic acid sequences encoding the monoclonal antibodies that bind HAV are produced and expressed in vitro in a host cell. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al,. *Cell* 30:295, 1982). Sequences encoding a monoclonal antibody that binds HAV can also be delivered to target cells in vitro via non-infectious systems, for instance liposomes. Thus disclosed herein are recombinant vectors that include nucleic acids encoding the proteins of monoclonal antibodies that bind HAV, and host cell transfected with the vectors.

In another specific, non-limiting embodiment, the variable regions of the monoclonal antibodies that bind HAV are encoded by the nucleic acid sequences as set forth in SEQ ID NO: 6, SEQ ID NO: 7, SEQ ID NO: 8, SEQ ID NO: 9

IV. Methods of Detecting Hepatitis A Virus (HAV)

Methods of detecting hepatitis A virus (HAV) are disclosed herein. In one embodiment, HAV is detected using a monoclonal antibody comprising the CDR3 region of the variable region as set forth in amino acids 100–113 of SEQ ID NO: 1, amino acids 100–113 of SEQ ID NO: 2, amino acids 101–126 of SEQ ID NO: 3, or amino acids 100–113 of SEQ ID NO: 4. In another embodiment the monoclonal antibody further comprises a CDR1 region of the variable region as set forth in amino acids 32–36 of SEQ ID NO: 1, amino acids 32–36 of SEQ ID NO: 2, amino acids 32–38 of SEQ ID NO: 3, or amino acids 32–36 of SEQ ID NO: 4. In yet another embodiment, the monoclonal antibody further comprises a CDR2 region of the variable region as set forth in amino acids 51–67 of SEQ ID NO: 1, amino acids 51–67 of SEQ ID NO: 2, amino acids 53–68 of SEQ ID NO: 3, or amino acids 51–67 of SEQ ID NO: 4. The monoclonal antibody can further comprise the variable region framework region (FR) sequences as provided in amino acids 1–31, 37–50, 68–99, and/or 114–124 of SEQ ID NO: 1, amino acids 1–31, 37–50, 68–99, and 114–124 of SEQ ID NO: 2, amino acids 1–31, 39–52, 60–100, and 127–137 of SEQ ID NO: 3, and amino acids 1–31, 37–50, 68–99, and 114–124 of SEQ ID NO: 4.

The monoclonal antibody can further comprise the variable region chain amino acid sequences as provided in SEQ ID NO: 1, SEQ ID NO: 2, SEQ ID NO: 3, or SEQ ID NO: 4, or a conservative variant or an antigen binding fragment thereof, or an amino acid sequence having at least, for example, 70%, 80%, 85%, 90%, 95% or even 98% sequence identity to SEQ ID NO: 1, SEQ ID NO: 2, SEQ ID NO: 3 or SEQ ID NO: 4.

The antibodies or antigen binding fragments of the antibodies are used as in vitro diagnostic agents to test for the presence of HAV in biological samples. For example, the novel specific binding molecules of the disclosure can be used in highly sensitive methods for screening and identifying individuals infected with HAV, as well as for screening for HAV-contaminated blood or blood products. The antibodies or antigen binding fragments can also be used in assays for monitoring the progress of anti-HAV therapies in treated individuals, and for monitoring the growth rate of HAV cultures used in research and investigation of the HAV agent.

In one embodiment, a sample such as biological fluid or tissue obtained from a subject is contacted with one or more of the antibodies or antigen binding fragments of the antibodies under conditions allowing the formation of an immune complex between the antibody or fragment and the HAV antigen that may be present in the sample. The formation of an immune complex indicates the presence of HAV in the sample. This complex is then detected by immunoassays. Such assays include, but are not limited to, radioimmunoassays, Western blot assays, immunofluorescent assays, enzyme immunoassays, chemiluminescent assays, immunohistochemical assays. In one embodiment, the antibody is labeled. The label may itself be detectable (e.g., radioisotope labels or fluorescent labels) or, in the case of an enzymatic label, may catalyze chemical alteration of a substrate compound or composition which is detectable. In another embodiment, the antibody or antigen binding fragment is detected by a second antibody that is labeled.

In one specific, non-limiting example, liver cells of a subject can also be assayed to detect known biochemical evidence of hepatitis A as a means of monitoring progression of the disease. For instance the presence of liver enzymes that are present in the blood of a subject suffering from hepatitis A, and which are markers of hepatic injury, may be assayed. Such biochemical indicators include the liver enzymes aspartate amino transferase (AST), alanine amino transferase (ALT) and gamma glutamyl transpeptidase (GGTP). Such monitoring can serve as a control by monitoring progression of the disease simultaneously with administration of the antibodies or antigen binding fragments of the antibodies.

V. Methods of Treating Hepatitis A

A treatment is disclosed herein for an infection with hepatitis A virus in a subject. In one embodiment, the subject is a mammal, for example a primate such as a human. Treatment includes both inhibition of initial infection (e.g., prophylactic treatment), and therapeutic interventions to alter the natural course of an untreated HAV infection. The method includes administering the antibodies or antigen binding fragments of the antibodies, and optionally one or more other pharmaceutical agents, to the subject in a pharmaceutically compatible carrier and in an amount effective to inhibit the development or progression of viral disease. In a specific, non-limiting embodiment, the pharmaceutical is an anti-viral agent and the virus is HAV. In some embodiments, the antibody neutralizes HAV in order to treat the patient. Although the treatment can be used prophylactically in any patient in a demographic group at significant risk for HAV, subjects can also be selected using more specific criteria (e.g., exposure to a contaminated water source or fecal material).

When supplied prophylactically, a pharmaceutical composition(s) of the disclosure is provided in advance of any exposure to any one or more of the HAV strains or in advance of any symptoms due to infection of the virus. Alternatively, prophylaxis can be administered after the exposure of a subject to the virus (for example, exposure to contaminated fecal material) to inhibit subsequent infection of the subject. The prophylactic administration of a pharmaceutical composition(s) of the disclosure serves to prevent, inhibit, or attenuate any subsequent infection of the virus in a subject. For therapeutic use, a pharmaceutical composition(s) of the disclosure is provided, for instance at (or shortly after) the onset of infection or alternatively at the onset of any symptom of infection or any disease or deleterious effects caused by these viruses. The therapeutic administration of the pharmaceutical composition(s) serves to attenuate the infection or disease. The pharmaceutical composition(s) of the present disclosure may, thus, be provided either prior to the anticipated exposure to the viruses of this disclosure or after the initiation of infection.

The vehicle in which the drug is delivered can include pharmaceutically acceptable compositions of the drugs, using methods well known to those with skill in the art. Any of the common carriers, such as sterile saline or glucose solution, can be utilized with the compositions provided by the disclosure. Routes of administration include but are not limited to oral and parenteral routes, such as intravenous (iv), intraperitoneal (ip), intramuscular (im), subcutaneous, rectal, topical, ophthalmic, nasal, and transdermal. In addition, a pharmaceutical composition(s) may be administered as an immunoprophylactic in a single dose schedule or as an immunotherapy in a multiple dose schedule. A multiple dose schedule is one in which a primary course of treatment may be with more than one separate dose, for instance 1–10 doses, followed by other doses given at subsequent time intervals as needed to maintain or reinforce the action of the compositions. Thus, the dosage regime will also, at least in part, be determined based on the particular needs of the subject to be treated and will be dependent upon the judgement of the administering practitioner.

Embodiments of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions.

The antibodies of the present disclosure are ideally administered as soon as possible after potential or actual exposure to the virus. Alternatively the agent may be administered, for example, following ingestion of contaminated foods. Alternatively, once HAV infection has been confirmed by clinical observation or laboratory tests, a therapeutically effective amount of antibodies or antigen binding fragments of the antibodies is administered. In one embodiment, the dose can be given by frequent bolus administration.

A therapeutically effective amount of a monoclonal antibody for individual patients may be determined by titrating the amount of antibody given to the individual to arrive at the therapeutic or prophylactic effect while minimizing potential side effects. In addition to antibodies comprising intact immunoglobulin molecules, substantially intact immunoglobulin molecules and portions of immunoglobulin molecules, and chimeric antibody molecules thereof, several therapeutically useful molecules are known in the art that include antigen-binding sites capable of exhibiting immunological binding properties of an antibody molecule. One specific, non-limiting example is a Fab molecule that includes a heterodimer including an intact antigen-binding site.

The amount of composition to be delivered depends on the subject being treated, the capacity of the subject's immune system to mount its own immune responses, and the degree of protection desired. The exact amount necessary will vary depending on the age and general condition of the individual to be treated, the severity of the condition being treated and the particular anti-HAV agent selected and its mode of administration, among other factors. One skilled in the art may readily determine an appropriate effective amount. Therefore, a therapeutically effective amount (e.g., a neutralizing amount) of the composition will be sufficient to bring about treatment, inhibition or prevention of hepatitis A disease symptoms. The effective amount may be determined by measuring the amount of HAV following administration of the composition. Levels of HAV may be measured by in vitro assays known in the art such as RT-PCR.

The disclosure additionally relates to anti-idiotypic antibodies to the monoclonal antibodies disclosed herein. In one embodiment, an anti-idiotypic antibody may be prepared by immunizing a host animal with a monoclonal antibody of the disclosure by methods known to those of skill in the art. To eliminate an immunogenic response to the Fc region, antibodies produced by the same species as the host animal may be used or the Fc region of the administered antibodies may be removed. The anti-idiotypic antibodies produced may be used to prepare pharmaceutical compositions rather than using the monoclonal antibodies of the disclosure.

In one embodiment, the antibodies or antigen binding fragments of the antibodies can be delivered to cells in the form of a nucleic acid that encodes the antibody, and is subsequently transcribed by the host cell. When using this method to deliver an antibody, a vector can be designed that contains a sequence encoding the antibody. The vector can also include a promoter to drive the expression of the antibody. In one embodiment, the vector is a viral vector. The viral vector including nucleic acid encoding the antibody can be delivered as a virion or in conjunction with a liposome. Several techniques for delivering therapeutic nucleic acid sequences are well known in the art for example, Blau and Springer, *New Engl. J. Med.* 333:1204–1207, 1995, and Hanania et al., *Amer. J. Med.* 99:537–552, 1995.

The present methods also include combinations of the monoclonal antibodies disclosed herein with one or more antiviral drugs useful in the treatment of hepatitis A. For example, the monoclonal antibodies disclosed herein may be administered, whether before or after exposure to the virus, in combination with effective doses of other anti-virals, immunomodulators, anti-infectives, or vaccines. The term "administration" refers to both concurrent and sequential administration of the active agents.

In one embodiment, a combination of monoclonal antibody that binds HAV with one or more agents useful in the treatment of hepatitis A is provided.

Examples of antivirals that can be used include: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo Alto, Calif.), didehydrodeoxythymidine or d4T (from Bristol-Myers-Squibb), EL10 (from Elan Corp. of Gainesville, Ga.), dideoxycytidine or ddC (from Hoffman-LaRoche), Novapren (from Novaferon Labs, Inc. of Akron, Ohio), zidovudine or AZT (from Burroughs Wellcome), ribavirin (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Examples of immuno-modulators are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, TNF (Genentech), and soluble TNF receptors (Immunex).

VI. Methods of Screening for Agents Useful for Prevention and Treatment of Hepatitis A The antibodies or antigen binding fragments disclosed herein are of use in in vitro assays for screening agents that bind HAV, or for measuring the affinity of an agent for HAV as a method for detecting an agent that inhibits HAV replication. In one specific, non-limiting example, an antibody or antigen binding fragment disclosed herein is contacted with HAV in the presence of an agent of interest. The ability of the virus to bind to the antibody or antigen binding fragment is then assessed. If, in the presence of the antibodies or antigen binding fragments of the antibodies, the agent being tested interferes with the antibody/antigen interaction, then the agent specifically binds HAV. Agents of interest include, but are not limited to polypeptides, isolated biological material, chemical compounds, pharmaceutical, or peptidomimetics.

In another embodiment, the antibody or antigen binding fragment is labeled. In other embodiments, antibodies or antigen binding fragments may be immobilized on a solid substrate and the HAV proteins labeled for detection. Suitable labels include, but are not limited to, enzymatic, fluorescent, or radioactive labels. Alternatively either the antibodies or antigen binding fragments of the antibodies are covalently linked to a biosensor chip. Samples containing HAV can then be passed over the chip. This type of assay can is readily adapted to high-throughput screening for either synthetic or natural compounds that interfere with the interaction of HAV and antibodies or antigen binding fragments of the antibodies.

VI. Kits for Detection of Hepatitis A Virus

The antibodies and antigen binding fragments described herein are ideally suited for the preparation of a kit. The kit can include a carrier means, such as a box, a bag, or plastic carton. In one embodiment the carrier contains one or more containers, for instance vials, tubes, and the like that include a sample of antibody or antigen binding fragment. In another embodiment, the carrier includes a container with an agent that affects antibody or antigen binding fragment, a buffer, or a vehicle for the introduction of the antibody or antigen binding fragment. Instructions can be provided to detail the use of the components of the kit, such as written instructions, video presentations, or instructions in a format that can be opened on a computer (e.g. a diskette or CD-ROM disk). These instructions indicate, for example, how to use the antibody or antigen binding fragment to detect and/or treat hepatitis A virus or how to use the antibody or antigen binding fragment to screen test agents of interest (such as antiviral drugs). In a further embodiment, one or more control peptides are provided for use in the antibody or antigen binding fragment detection reactions.

The amount of each antibody or antigen binding fragment supplied in the kit can be any appropriate amount, depending for instance on the market to which the product is directed. For instance, if the kit is adapted for research or clinical use, the amount of each antibody or antigen binding fragment provided would likely be an amount sufficient to screen several biological samples. The antibodies or antigen binding fragments can be provided suspended in an aqueous solution or as a freeze-dried or lyophilized powder, for instance. In certain embodiments, the antibodies or antigen binding fragments will be provided in the form of a pharmaceutical composition. In other embodiments, nucleic acids encoding the antibodies of the disclosure are provided.

Those of ordinary skill in the art know the amount of antibody or antigen binding fragment that is appropriate for use in a single detection reaction. General guidelines may for instance be found in Harlow and Lane, Antibodies, A Laboratory Manual, Cold Spring Harbor, N.Y., 1988), Sambrook et al. (In Molecular Cloning: A Laboratory Manual, Cold Spring Harbor, N.Y., 1989), and Ausubel et al. (In Current Protocols in Molecular Biology, Greene Publ. Assoc. and Wiley-Intersciences, 1992).

Without further elaboration, it is believed that one skilled in the art can, using this description, utilize the present disclosure to its fullest extent. The following examples are illustrative only, and not limiting of the remainder of the disclosure in any way whatsoever.

EXAMPLES

Example 1

Construction of γ1/k Antibody Phage Library

Chimpanzees are susceptible to infection with HAV and can produce antibodies that neutralize the virus. Chimpanzee immunoglobulins are virtually identical to those of humans; thus, they have the same potential as human antibodies for clinical applications. The construction and use of a bone marrow-derived cDNA library of antibody genes displayed as Fab fragments on the surface of bacteriophage particles for the isolation of chimpanzee monoclonal antibodies to the HAV capsid is described herein. These MAbs may be useful in further defining the properties of neutralizing antibodies that prevent hepatitis A as well as for clinical applications.

Bone marrow was aspirated from the iliac crest of a chimpanzee that had been experimentally infected with the five recognized hepatitis-causing viruses, hepatitis A, B, C, D. and E viruses. Aspiration took place 6 years post-infection and three weeks prior to the bone marrow aspiration, the animal had been boosted with hepatitis A vaccine. The animal was maintained in an approved facility under conditions that met or exceeded all requirements for animal use.

The bone marrow lymphocytes were purified on a Ficoll gradient and stored as a viable single-cell suspension in 10% dimethyl sulfoxide-10% fetal calf serum-RPMI 1640 medium (BioWhittaker) in liquid nitrogen. Total RNA was extracted from ~10e8 bone marrow lymphocytes (RNA Isolation Kit; Stratagene), and mRNA was reverse transcribed into cDNA using an oligo(dT) primer (Gibco/BRL). The cDNAs were amplified by PCR using rTth DNA polymerase (Perkin-Elmer). Thirty cycles of 94° C. for 15 s, 52° C. for 50 s, and 68° C. for 90 s were performed. Chimpanzee γ1-chain genes were amplified using primers specific for the human-chain genes. Fd segments (variable and first constant domains) of the chimpanzee γ1-chain genes were amplified with nine family-specific human VH primers recognizing the 5' end of the genes and a chimpanzee γ1-specific 3' primer (5'-GCATGTACTAGTTGTGTCACAAGATTTGGG-3', SEQ ID NO: 5) (See Barbas, et al., *Proc. Natl. Acad. Sci U.S.A.* 88:7978-7982, 1991 and Schofield, et al., *J. Virol.* 74(12): 5548-55, 2000).

The amplified chains were cloned into the pComb3H phage display vector. The amplified γ1 chains were cloned into the pGEM-T cloning vector (Promega), transformed into *Escherichia coli* XL-1 Blue (Stratagene), and expanded into a volume of 2 liters by solid-phase amplification as described by Glamann et al., *J. Virol.* 72:585-592, 1998.

The γ1-pGem-T library was digested with XhoI and SpeI (Boehringer Mannheim) and ligated into the κ-chain pComb3H library, also digested with XhoI and SpeI. The ligated products were transformed into *E. coli* XL-1 Blue. Transformants were expanded into a volume of 2 liters by solid-phase amplification. The final library of 1.9e7 clones was stored in 12.5% glycerol-Luria-Bertani (LB) broth at 80° C. until use.

Example 2

Isolation of HAV-Specific Fabs and Sequence Analysis

Screening of the combinatorial library was carried out as described in Barbas, et al., *Proc. Natl. Acad. Sci. U.S.A.* 88:7978-7982, 1991; Schofield et al., *J. Virol.* 74(12): 5548-55, 2000; and Williamson et al., *Proc. Natl. Acad. Sci. U.S.A.* 90(9): 4141-5, 1993. Three rounds of panning were performed on formalin-inactivated HM-175-coated ELISA wells. Three hundred clones were analyzed for HAV-specificity by ELISA. Twenty-four clones were determined to be HAV-specific. Fabs were detected by enzyme-linked immunosorbant assays (ELISA) with goat anti-human IgG (H+L)-specific antibody (Pierce). The antibody was coated on EIA/RIA A/2 plates (Costar) overnight at 4° C. at a dilution of 1:1000, in 50 mM sodium carbonate buffer (pH 9.6). In all panning experiments and other ELISAs, formalin-inactivated HAV particles (HM-175 strain; Viral Antigens Inc.)

were diluted 1:2 in 50 mM sodium carbonate buffer (pH 9.6), and coated on microtiter wells as above.

The restriction enzyme Bst NI (New England Biologicals) cuts frequently in the human γ1-heavy chain (See Marks et al., *J. Mol. Biol.* 222(3):581–97, 1001). This enzyme was used to screen for different heavy-chain sequences among the Fab clones by fingerprinting with the restriction enzyme. One microgram of plasmid DNA was digested with 1 U of enzyme overnight at 60° C. The restriction digests were analyzed on a 3% agarose gel. Nucleic acid sequencing was performed with the ABI PRISM Dye Terminator Cycle Sequencing Ready Reaction kit with Ampli-Taq DNA Polymerase (Perkin-Elmer) and the sequencing primers HC1 and HC4 for the heavy-chain and LC1 and LC4 for the k-chain (See Glamann et al., *J. Virol.* 72:585–592, 1998). Sequences were analyzed with GeneWorks (Oxford Molecular Group) software package. Sequence similarity searches were performed with the V-BASE program, which is a compilation of all available human variable segment Ig germ line sequences (See Cook and Tomlinson, *Immunol. Today* 16(5): 237–42, 1995).

Several different digestion patterns were observed, suggesting that more than one heavy chain sequence was present. Single colonies were picked and Fab production was induced as described in Glamann et al., *J. Virol.* 72: 585–592, 1998. Protein concentrations were determined both by dye binding assay (Bio-Rad) and A280 nm (using the extinction co-efficient of 1.4 optical density units equivalent to 1.0 mg ml-1). The Fab purity was determined by polyacrylamide gel electrophoresis followed by colloidal coomassie blue staining (Sigma). Where required, the purified Fabs were diluted in sodium bicarbonate buffer (pH 9.0), and biotinylated at 4° C. as per the manufacturer's protocol (Pierce). After biotinylation, the Fabs were dialyzed against phosphate-buffered saline (PBS, pH 7.4) overnight at 4° C., and concentrated in Centricon-30 concentrators (Amicon) as required.

Sequence analysis was performed on thirteen of the twenty-four clones. From these thirteen clones, four unique γ1-heavy chains were identified. They were represented by clones HAV#4, HAV#5, HAV#6 and HAV#14 (FIG. 1). The amino acid sequences of the variable regions of these clones are as set forth in SEQ ID NO: 1, SEQ ID NO: 2, SEQ ID NO: 3 and SEQ ID NO: 4, respectively.

Table 1 sets forth the classification of the specific germline origin of the four clones based on a sequence similarity search of all the known human immunoglobulin genes.

TABLE 1

Classification of chimpanzee γ1-chains of the four HAV-specific MAbs, based on nucleotide sequence homology with human immunoglobulin germ line genes.

| MAb | $V_H$ family | $V_H$ segment | D segment | $J_H$ segment |
|---|---|---|---|---|
| HAV#4 | VH1 | DP-25[1] | D1-7[2] | JH3b |
| HAV#5 | VH5 | DP-73[1] | D4-11[2] | JH6c |
| HAV#6 | VH4 | DP-78[3] | D1-1[2] | JH6c |
| HAV#14 | VH5 | DP-7[3] | ND | JH6c |

ND—not determined due to lack of identifiable homologue
[1](Tomlinson et al., 1992)
[2](Corbett et al., 1997)
[3]V-BASE database Example 3

Neutralization of HAV strain HM-175

The ability of the four MAbs, as Fab fragments, to neutralize HAV in vitro was determined by a modified radioimmunofocus assay (RIFA) as described by Raychaudhuri et al., *J. Virol.* 72(9): 7467–76, 1998. Briefly, chloroform-extracted HAV was mixed with antibody diluted in 10% BSA/PBS, and incubated for 2 hours at room temperature. Log10 dilutions of the virus-antibody mixtures were inoculated onto confluent monolayers of fetal rhesus kidney (subclone 11–1) cells grown on 25 mm diameter Thermonox plastic coverslips (fixed to the bottom of each well) for 1 hour at 34.5° C. in a CO2 incubator. The infected cells were then overlaid with 0.5% agarose-MEM supplemented with glutamine, gentamycin and 2% FCS, and incubated for 10 to 14 days at 34.5° C. The cell monolayers were fixed with acetone, air dried and stored at −20° C. until stained. HAV foci were reacted with a 1:500 dilution of chimpanzee 1442 antisera for 30 minutes at 34.5° C. The cells were washed three times in PBS-glycine, and then incubated with $^{125}$I-labelled sheep anti-human IgG F(ab')2 fragment (1.0 mCi/ml; Amersham) for 1 hour at 34.5° C. After four washes, the coverslips were air dried, and exposed to X-ray film (Kodak) at −70° C.

The HAV strain used in the neutralization assay, HM-175, was the same as the panning antigen. The virus was mixed individually with each of the four purified Fabs, incubated at room temperature for 2 hours, then serial 10-fold dilutions were inoculated onto confluent 11-1 cell monolayers. The monolayers were overlaid with medium containing agarose and incubated at 34.5° C. After 10 days, the cells were fixed, stained and the foci of infected cells were detected by autoradiography. In the developed autoradiograph, areas representing wells were examined for a positive signal indicating the presence of infected cells. A Fab was considered "neutralizing" if the autoradiograph area representing a well contained a reduced number of foci. In this case, Fabs HAV#4, HAV#5, HAV#6, HAV#14 and mouse MAb K3-2F2 neutralized the HM-175 strain of HAV. MAb HBV#8 and the control lacking antibody, included as negative controls, did not neutralize the HM-175 strain of HAV.

Example 4

Neutralization of the Simian HAV Strain AGM-27

The AGM-27 strain is one of the most divergent HAV strains identified thus far (See Tsarev et al., *J. Gen. Virol.* 72(7): 1677–83, 1991). The capsid proteins contain twenty-eight amino acid changes compared to the human strain HM-175 (1 amino acid change in VP4, 6 in VP2, 7 in VP3 and 14 in VP1). These amino acid changes include one of the two mutations identified in VP3 and two of the four amino acid mutations identified in VP 1 as being involved in virus escape from neutralizing mouse MAbs (See Ping et al., *Proc. Natl. Acad. Sci. U.S.A.* 85(21): 8281–5, 1988; Ping et al., *J. Virol.* 66(4): 2208–16, 1992; Stapleton and Lemon, *J. Virol.* 61(2): 491–8, 1987).

The ability of the four Fabs to neutralize AGM-27 was determined by RIFA. Each of the four Fabs was incubated with virus, and the mixtures were serially diluted prior to inoculation onto 11-1 cells. After 14 days incubation at 34.5° C., the cells were fixed and the RIFA was performed. Four well-characterized mouse MAbs were used as controls (See MacGregor et al., *J. Clin. Microbiol.* 18(5): 1237–43, 1983).

Mouse MAbs K2-4F2, K3-2F2 and B5B3 did not neutralize the AGM-27 strain, whereas mouse MAb K3-4C8 did neutralize the AGM-27 strain as previously reported by Tsarev et al. (See Tsarev et al., *J. Gen. Virol.* 72(7):1677–83, 1991). The negative control was the AGM-27 was the strain of HAV without antibody. The AGM-27 well (negative control) indicated a positive signal, corroborating the results. The foci of infected cells were detected by autoradiography. In the developed autoradiograph, areas representing wells were examined for a positive signal indicating the presence of infected cells. A Fab was considered "neutralizing" if the autoradiograph demonstrated a reduced number of foci. Of the chimpanzee Fabs, HAV#4 and HAV#6 neutralized the AGM-27 strain but HAV#5 and HAV#14 did not. Furthermore, HAV#4 and HAV#6 bound to viral antigen in 11-1 cells infected with AGM-27 as assayed by immunofluorescence microscopy. However, neither HAV#5 nor HAV#14 bound to antigen in this assay as compared to the control (AGM-27).

Example 5

Neutralization of an HM-175 VP3-070 Mutant

Neutralization escape mutants generated in the presence of the mouse MAb K2-4F2 usually result in an amino acid change of Asp70→Ala70 in the VP3 capsid protein (See Nainan, *Virology* 191(2): 984–7, 1992; Ping et al., *Proc. Natl. Acad. Sci. U.S.A.* 85(21): 8281–5, 1988; Ping et al., *J. Virol.* 66(4): 2208–16, 1992). This mutation is also present in the VP3 protein of the AGM-27 strain. Because HAV#5 and HAV#14 did not neutralize the AGM-27 strain, a test was performed for neutralization of an HM-175 variant that had the VP3 Asp70→Ala70 mutation but otherwise was identical to the HM-175 strain. The neutralization assays were performed as described in Example 3. In the developed autoradiograph, areas representing wells were examined for a positive signal indicating the presence of infected cells. A Fab was considered "neutralizing" if the autoradiograph demonstrated a reduced number of foci. In this case, Fabs HAV#4, HAV#5, HAV#6, and HAV #14 neutralized the HM-175 VP3-070 mutant. The control murine MAb K2-4F2 did not. The VP3-070 well (negative control) indicated a positive signal, corroborating the results.

Example 6

Epitope Mapping with Fabs

Indirect competition ELISAs were performed to determine whether the four Fabs recognized similar or overlapping epitopes on the HAV capsid. The competing MAbs were titrated on HM-175-coated wells to determine the dilution that gave an O.D. reading of approximately 1.0 at A405 nm, and did not saturate the antigen coated to the plate. For the competition assay, three-fold dilutions of unlabeled MAbs were incubated in HM-175-coated wells for 1 hour at 37° C., then washed four times with PBS-Tween 20. A single dilution of the competing MAb (biotinylated Fab, whole IgG or mouse IgG) was incubated in all wells for 1 hour at 37° C. After four washes with PBS-Tween 20, the binding of the competitor MAb was detected with either streptavidin-alkaline phosphatase (Pierce), anti-human IgG (Fc-specific) alkaline phosphatase-conjugated antibody (Sigma) or anti-mouse IgG (H+L chain specific) alkaline phosphatase-conjugated antibody (Pierce).

Table 2 lists the percentage inhibition of antibody binding in each well that was previously coated with HM-175.

TABLE 2

Indirect competition assay data using Fabs HAV#4, HAV#5, HAV#6, and HAV#14 to block the binding of biotinylated chimpanzee Fabs and mouse MAbs K2-4F2, K3-2F2, and K3-4C8.

| | 2nd MAb (biotinylated) | | | | | | |
|---|---|---|---|---|---|---|---|
| 1st MAb | HAV#4 | HAV#5 | HAV#6 | HAV#14 | K3-2F2 | K3-4C8 | K2-4F2 |
| HAV#4 | 85[†] | 86 | 35 | 94 | 50 | 97 | 52 |
| HAV#5 | 87 | 89 | 53 | 94 | 64 | 97 | 63 |
| HAV#6 | (6)[‡] | 28 | 92 | (10) | 48 | 61 | 48 |
| HAV#14 | 65 | 61 | 22 | 81 | 51 | 84 | 49 |

[†]percentage inhibition of antibody binding to HM-175-coated wells
[‡]number in parentheses indicates percentage enhancement of antibody binding to HM-175-coated wells Unlabeled HAV#4, HAV#5 and HAV#14 blocked the binding of biotinylated HAV#4, HAV#5 and HAV#14 by >60%. Therefore, these three Fabs recognize the same or overlapping epitopes on the HAV capsid. Unlabeled HAV#6 did not significantly block the binding of the other three biotinylated Fabs and vice versa. Therefore, HAV#6 recognized an epitope on the HAV capsid distinct from that recognized by any of the other three Fabs. Indirect competition assays were also performed with the four Fabs and three well-characterized mouse MAbs (Table 2). The binding of MAbs K3-2F2 and K2-4F2 was inhibited approximately 50–60% by each of the four Fabs. Binding of MAb K3-4C8 to HM-175-coated wells was inhibited 84% by HAV#4, HAV#5 and HAV#14. This suggested that these three Fabs and mouse MAb K3-4C8 recognized either the same epitope or an overlapping epitope. HAV#6 inhibited K3-4C8 binding by 61% suggesting that the two corresponding epitopes overlap to some extent or are at least spatially close together on the HAV capsid. Table 3 summarizes the neutralization assay data for the monoclonal antibodies screened.

TABLE 3

Summary of neutralization assay data for chimpanzee MAbs HAV#4, HAV#5, HAV#6 and HAV#14, and mouse MAbs K2-4F2, K3-2F2, K3-4C8, and B5B3.

| | Neutralization | | |
|---|---|---|---|
| Antibody | HM-175 | VP3-070 | AGM-27 |
| HAV#4 | Yes | Yes | Yes |
| HAV#5 | Yes | Yes | No |
| HAV#14 | Yes | Yes | No |
| HAV#6 | Yes | Yes | Yes |
| K2-4F2 | ND[†] | No | No |
| K3-4C8 | ND | ND | Yes |
| K3-2F2 | Yes | ND | No |
| B5B3 | ND | ND | No |

[†]ND, not determined

Example 7

Epitope Mapping With IgGs

Indirect competition ELISAs were performed between the chimpanzee MAbs as whole IgG molecules and the mouse MAbs K3-2F2, K3-4C8, K2-4F2 as described in Example 5 (Also see MacGregor et al., *J. Clin. Microbiol.* 18(5): 1237–43, 1983) and mouse MAb B5B3 (Biogenesis). Whole IgGs were tested to overcome any differences in antibody affinity that may have arisen from comparing monovalent chimpanzee Fab fragments and bivalent mouse IgG molecules. Use of this protocol excludes differences in steric hindrance due to molecular size disparities between Fab and IgG molecules. In this example, the assay was performed in reverse with the mouse MAbs used to block the binding of the four chimpanzee IgG MAbs. Mouse MAb K3-4C8 reduced the binding of HAV#4, HAV#5 and HAV#14 IgG to approximately 20–40% of the respective controls. Mouse MAbs K3-2F2, K2-4F2 and B5B3 could only reduce binding of HAV#4, HAV#5 and HAV#14 IgG to a maximum of 60%, compared to the respective controls.

Table 4 summarizes the competition assay data for the monoclonal antibodies screened. Within the context of each assay, antibodies were described as "competing" when >60% inhibition of binding was observed, i.e. the two epitopes recognized were likely to be the same or to overlap extensively. However, an antibody described as "non-competing" did not necessarily mean no competition between an antibody pair occurred, rather that there was less extensive overlap between two epitopes.

TABLE 4

Summary of epitope mapping data for chimpanzee MAbs HAV#4, HAV#5, HAV#6 and HAV#14, and mouse MAbs K2-4F2, K3-2F2, K3-4C8, and B5B3.

| Antibody | Epitope-mapping[‡] | | | |
|---|---|---|---|---|
| | HAV#4* | HAV#5 | HAV#14 | HAV#6 |
| HAV#4 | Yes | Yes | Yes | No |
| HAV#5 | Yes | Yes | Yes | No |
| HAV#14 | Yes | Yes | Yes | No |
| HAV#6 | No | No | No | Yes |
| K2-4F2 | No | No | No | No |
| K3-4C8 | Yes | Yes | Yes | No |
| K3-2F2 | No | No | No | No |
| B5B3 | No | No | No | No |

*competition assays among the four chimpanzee MAbs were performed with Fab fragments; competition assays between the chimpanzee MAbs and the mouse MAbs were performed with whole IgG molecules.
[‡]"Yes" is defined as >60% inhibition of binding to HM-175-coated ELISA wells for each antibody pair.

FIG. 2 summarizes the results of an exemplary indirect competition assay between HAV#4 IgG, and the mouse MAbs, K3-2F2, K3-4C8, K2-4F2, and B5B3. Similar assays were conducted using HAV#5, HAV#6 and HAV#14. Mouse MAbs K3-2F2, K2-4F2 and B5B3 could only reduce binding of HAV#4, HAV#5 and HAV#14 IgG to a maximum of 60%, compared to the respective controls. All four mouse MAbs had little effect upon the binding of HAV#6 IgG to HM-175-coated wells. HAV#6 IgG binding was reduced maximally to 60% of the control. These data confirmed those obtained with the Fab fragments.

Example 8

Cell Receptor-Blocking Assay

Indirect competition assays were performed to determine whether HAV #4, HAV#5, HAV#6 and HAV#14 could inhibit virus-cell receptor interaction. HM-175-coated wells were incubated with the Fabs prior to the addition of the soluble HAV cell receptor, HAVCR1, derived from African green monkey kidney cells (See Silberstein, et al., *J. Virol.* 75(2): 717–25, 2001). A range of dilutions of the soluble simian cell receptor for HAV, HAVCR1 was incubated in HM-175-coated wells for 1 hour at 37° C. After washing, a constant amount of MAb was added to the wells, and incubated for 1 hour at 37° C. The bound antibody was detected with an anti-human IgG Fab-specific alkaline phosphatase-labeled secondary antibody (1:5000). The optical density was measured at 405 nm with a reference wavelength of 650 nm.

Figure 3:
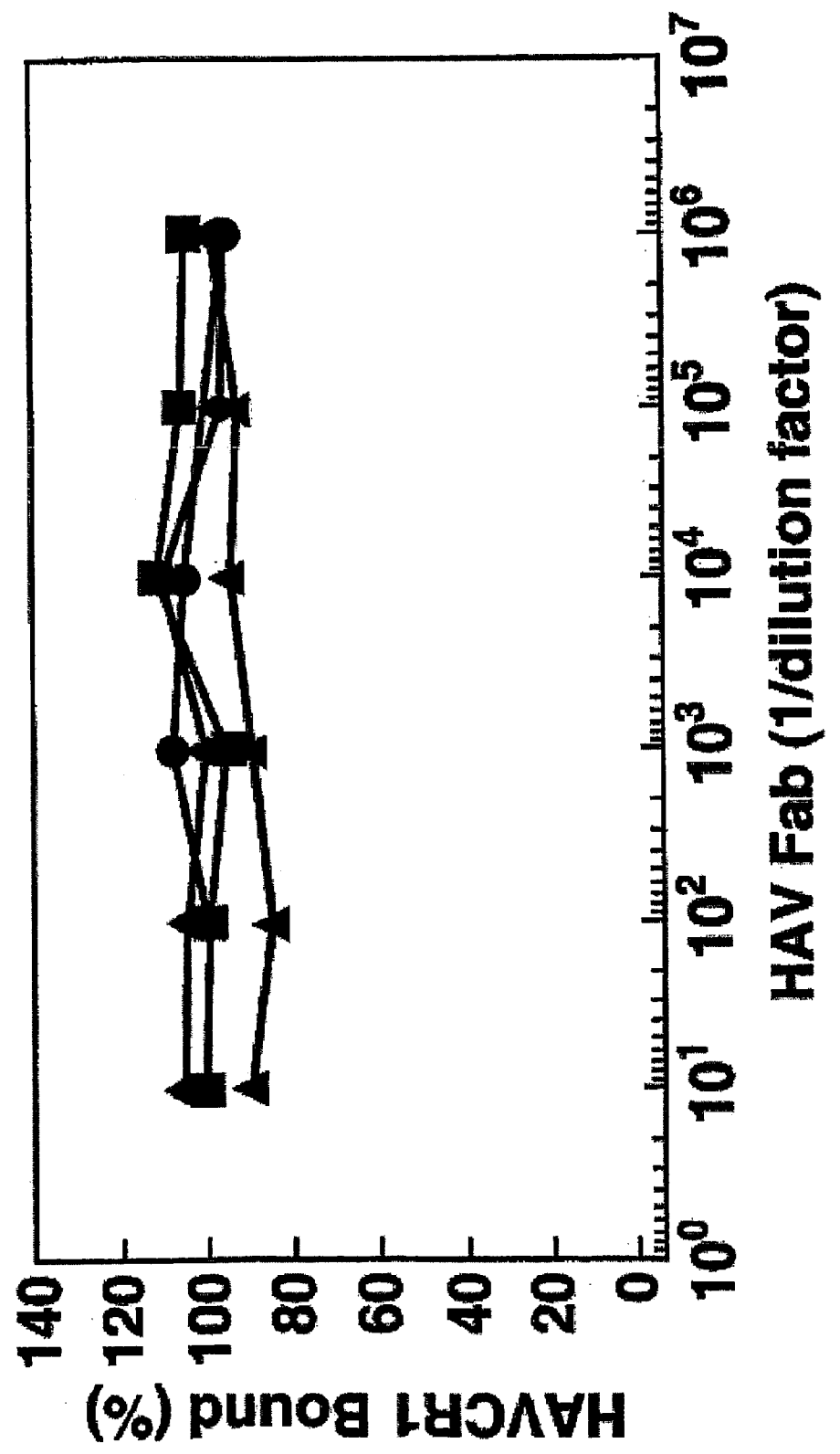

Blocking of receptor binding to the HM-175 was not observed. FIG. 3 summarizes the results of the cell receptor-blocking assay described herein. For use in a reciprocal assay, HAVCR1 was provided as a fusion protein with the human IgG Fc region. In that assay, binding was detected with an anti-human IgG (Fc-specific) alkaline phosphatase-labeled secondary antibody (1:5000). HAVCR1 was unable to inhibit the binding of any of the Fabs to HM-175-coated wells. A reciprocal assay was also repeated with the chimpanzee MAbs as whole IgGs. Again inhibition was not observed with either IgG or HAVCR1 as the blocking agent.

Example 9

Conversion of Fab to Whole IgG Molecules and Expression in COS-7 Cells

The heavy- and light-chain genes of the MAbs were sub-cloned into pFab-CMV using the same restriction enzyme sites used to clone the heavy- and light-chain genes into the phage display vector, pComb3H (See Sanna et al., *Immunotechnology* 4(3–4): 185–8, 1999). After confirming the sequence of each clone, whole IgGs were obtained from tissue culture supernatants five days post-transfection of confluent COS-7 cells in T-75 flasks (Costar). Transfection of the plasmid DNAs was performed with Superfect transfection reagent (Qiagen) according to the manufacturer's instructions.

The cDNA library used to isolate the antibodies to HAV is a potential repository for antibodies to all five recognized human hepatitis viruses, HAV, HBV, HCV, HDV and HEV, since the donor chimpanzee had been experimentally infected with each of the hepatitis viruses. In the first analysis of the library, two neutralizing MAbs directed to the putative HEV capsid protein were identified (Schofield et al., *Journal of Virology* 74(12), 5548–5555, 2000, see also U.S. patent application Ser. No. 10/148,737, PCT Application No. US00/32614 and U.S. Provisional Patent Application No. 60/167,490, each of which is expressly incorporated herein). In this second analysis of the library, four MAbs directed to the HAV capsid were identified. The γ1-heavy chains of the HAV MAbs were most closely related, at the nucleotide level, to γ1-heavy chains from the human VH1, VH4 and VH5 gene families; such chimpanzee-derived immunoglobulin sequences differ from human-derived sequences no more than genetically distinct human sequences differ from each other. Furthermore, human-derived immunoglobulins exhibit the same half-life in chimpanzees as they do in humans, suggesting that human antibodies are recognized as self and not foreign antigens.

Competition assays suggested the MAbs recognized more than one epitope on the HAV capsid since the three MAbs competed strongly with each other (HAV#4, HAV#5 and HAV#14) for binding but the fourth (HAV#6) competed poorly. All four MAbs neutralized the HAV strain HM-175, the same strain used as the panning antigen. Two of the four MAbs also neutralized the divergent AGM-27 strain and two did not. This, taken with the competition assay data, indicated that there were at least three different epitopes recognized by the four MAbs. Of the three MAbs which competed with each other, HAV#4 recognized a unique epitope since the MAb neutralized both HM-175 and AGM-27 whereas a different epitope was recognized by HAV#5 and HAV#14 since these two MAbs neutralized HM-175 but not AGM-27; the non-competing MAb, HAV#6, recognized a third epitope (this MAb neutralized both HM-175 and AGM-27).

Figure 4:
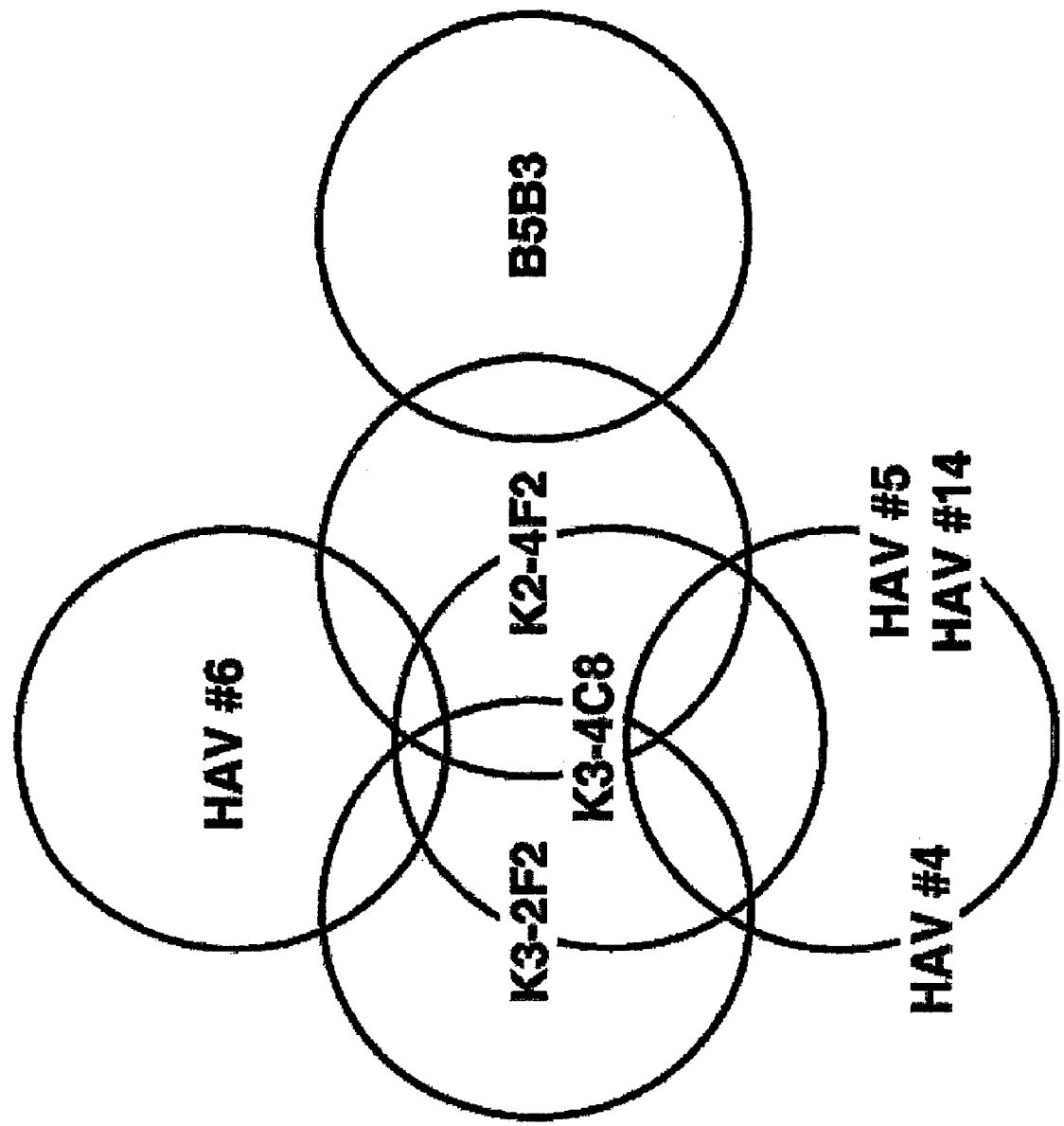
FIG. 4 is a digital image showing the predicted topography of the epitopes recognized by four chimpanzee MAbs, HAV#4, HAV#5, HAV#6 and HAV#14 within the context of the topography of epitopes characterized by mouse MAbs K3-4C8, K2-4F2, K3-2F2 and B5B3 (Ping et al., *Proc. Natl. Acad. Sci. U.S.A.* 85(21): 8281–5, 1988, Ping et al., *J. Virol.* 66(4): 2208–16, 1992; MacGregor et al., *J. Clin. Microbiol.* 18(5): 1237–43, 1983). Overlap between any two circles indicates >50% inhibition of binding. HAV#4, HAV#5 and HAV#14 epitopes are represented by a single circle, however HAV#4 splits into a different group based upon its ability to neutralize the simian HAV strain, AGM-27.

Competition assays were performed with the four chimpanzee MAbs, as both Fabs and whole IgG molecules, and the mouse MAbs K3-2F2, K3-4C8, K2-4F2, and B5B3. A topographical map of the antibody epitopes recognized by the murine and chimpanzee MAbs based on our competition data and other published data (see Ping et al., *Proc. Natl. Acad. Sci. U.S.A.* 85(21), 8281–8285, 1988; Ping and Lemon, *J. Virol.* 66(4), 2208–2216, 1992; Stapleton and Lemon, *J. Virol.* 61(2), 491–498, 1987) (see FIG. 4). In accordance with previously published data, the epitopes are closely spaced; the majority of the chimpanzee MAb epitopes are shown closely overlapping with that of the murine MAb K3-4C8. The competition and neutralization data (summarized in Table 3) suggested that MAb K3-4C8 and HAV#4 either recognized the same epitope or two epitopes that overlap extensively. In contrast, the data overall suggested that the other three chimpanzee MAbs (HAV#5, HAV#6, HAV#14) recognize epitopes different from those recognized by the majority of neutralizing murine MAbs. Since escape mutants implicated VP3-070, VP1-102, and VP1-221 as critical for neutralization by the murine MAbs, it can be presumed that these amino acids are not components of the epitopes recognized by the chimpanzee MAbs. Indeed, VP3-070 has been experimentally excluded since all four chimpanzee MAbs neutralized the HM-175 VP3-070 mutant and two MAbs, HAV#4 and HAV#6, neutralized the AGM-27 virus which also has the VP3-070 mutation. The fact that AGM-27 was not neutralized by HAV#5 or HAV#14 means that one or more of the amino acids differentiating the capsid proteins of the HM-175 and AGM-27 strains must be critical for epitope recognition by these antibodies: this narrows the possibilities down to only 27 amino acids after the VP3-070 amino acid is excluded.

HAV#6 neutralized both the HM-175 VP3-070 mutant virus and the simian HAV strain AGM-27. Therefore, HAV#6 appears to recognize a novel epitope on the HAV capsid that is not defined by any of the amino acid differences between HM-175 and AGM-27.

It is conceivable that the two sets of antibodies (murine and chimpanzee) are directed to distinct epitopes on the HAV capsid because of differences in antigen processing by the mouse and chimpanzee antigen-presenting cells (e.g. for poliovirus, see Uhlig and Dernick, *Virology* 163(1), 214–217, 1988). However, competition studies with murine anti-HAV MAbs and anti-HAV positive human sera suggest that this is not the case for HAV (Ping and Lemon, 1992). The results may also reflect differences in the affinities for the HAV capsid of these two sets of MAbs (murine and chimpanzee).

Convalescent human anti-HAV, in the form of normal immune globulin, has been used as a pre-exposure and post-exposure immunoprophylactic agent against hepatitis A. In recent years its use has diminished because of its unavailability and because licensed hepatitis A vaccines have replaced it for most pre-exposure applications. However, vaccination requires a minimum of two weeks to achieve protection and post-exposure prophylaxis therefore continues to be a legitimate application for immune globulin. In addition, there are other potential uses for such globulin: fulminant hepatitis A has been reported to account for up to 10–20% of liver transplants in children in some countries (Ciocca, *Vaccine* 18 Suppl. 1, S71–74 2000) and to be more common in adults who have coexisting liver disease (Lefilliatre and Villeneuve, *Can. J. Public Health* 91(3), 168–167, 2000; O'Grady, *J. Viral Hepat.* 7 Suppl. 1, 9–10, 2000; Vento, *J. Viral Hepat.* 7 Suppl. 1, 7–8, 2000). Also, although normally self-limiting, HAV infection can cause persistent or relapsing hepatitis, especially in those who are immunosuppressed; recurrent hepatitis A has been reported following liver transplantation for fulminant disease (Gane et al., *J. Med. Virol.* 45(1), 35–39, 1995). This has prompted the suggestion that HAV-specific immune globulin be given at the time of transplantation for HAV-induced acute liver failure to prevent such recurrences (Gane et al., *J. Med. Virol.* 45(1), 35–39, 1995). Thus, there continue to be potential clinical applications for a broadly-reactive and potent hepatitis A immune globulin. Immunoglobulin derived from the MAbs described herein could be used for preventing and possibly treating hepatitis A.

Thus, four chimpanzee MAbs to the HAV capsid, which were generated from a library of antibody genes amplified by PCR with human heavy- and light-chain gene-specific primers have been characterized. The competition data with previously well-characterized murine MAbs suggests there is a single immunodominant antigen site on the HAV capsid. The MAbs competed with one of the murine MAbs that were used to define this site. However, at least three of our chimpanzee MAbs appear to be directed to epitopes that are previously undefined.

Example 10

Measurement of in Vitro Neutralization of HAV by in Vivo Monitoring

A chimpanzee infection dose (CID50) is the dose that infects 50% of chimpanzees upon exposure. Sixty-four 50% chimpanzee infectious doses of HAV, strain HM-175, are incubated overnight at 4° C., with a mixture of monoclonal antibodies or antigen binding fragments of the antibodies against HAV. The next morning the mixture is inoculated intravenously into a naïve chimpanzee. The chimpanzee is followed weekly for biochemical evidence of hepatitis (e.g. altered concentrations of the liver enzymes ALT, ICD and GGTP), virologic evidence of infection and serologic evidence of antibody to HAV. If the chimpanzee remains free of evidence of HAV infection for six months, the experiment is repeated with a subset of the original pool of monoclonal antibodies. This procedure is repeated with different subsets of the monoclonal antibodies until the chimpanzee is infected. If necessary, additional chimpanzees are inoculated in order to determine exactly which monoclonal antibodies are neutralizing. If all of the monoclonal antibodies prove to be neutralizing, the procedure will be repeated with monoclonal antibodies directed against other viruses as a positive control for susceptibility of the chimpanzee.

Example 11

Passive Immunoprophylaxis against HAV

A naïve subject, such as a chimpanzee is infused intravenously with one or more neutralizing HAV monoclonal antibodies or modified or derivatized antigen binding fragments of the antibodies. The chimpanzee is challenged intravenously with sixty-four CID50 doses of HAV. The chimpanzee is followed weekly for six months and monitored for biochemical evidence of hepatitis (e.g. ALT, ICD, GGTP levels are monitored until the HAV antibody is no longer detectable), virologic evidence of infection, and the titre antibody to HAV (rising or falling antibody titre). If the chimpanzee remains free of disease, passive immunoprophylaxis is successful.

Example 12

Passive Immunoprophylaxis against HAV

A human subject at risk of infection with HAV is infused intravenously with one or more neutralizing HAV monoclonal antibodies or modified or derivatized antigen binding fragments of the antibodies. The subject is challenged intravenously with 64 $CID_{50}$ doses of HAV. The subject is monitored for biochemical evidence of hepatitis (e.g. ALT, ICD, GGTP), virologic evidence of infection, and the titre antibody to HAV (rising or falling antibody titre). If the subject remains free of disease, passive immunoprophylaxis is successful.

Example 13

Treatment of Subject with Hepatitis A

A human subject having hepatitis A is treated by administration of a therapeutically effective amount of the antibodies or antigen binding fragments of the antibodies. The subject is monitored for biochemical evidence of hepatitis A (e.g. ALT, ICD, GGTP), virologic evidence of infection and serologic evidence of antibody to HAV. If an index of the subject's condition improves (e.g., lowered viral load, lowered levels of markers of hepatic injury such as ALT/ICD/GGTP, etc.), treatment is successful.

It will be apparent that the precise details of the methods described may be varied or modified without departing from the spirit of the described disclosure. We claim all such modifications and variations that fall within the scope and spirit of the claims below.

We claim:

1. A monoclonal antibody or antigen binding fragment thereof, wherein the variable region of the monoclonal antibody comprises a CDR1 region comprising amino acids 32–38 of SEQ ID NO: 3, a CDR2 region comprising amino acids 53–68 of SEQ ID NO: 3, and a CDR3 region comprising amino acids 101–126 of SEQ ID NO: 3 wherein the antibody or antigen binding fragment thereof specifically binds hepatitis A virus.

2. The antibody of claim 1, further comprising a framework region having a sequence as set forth as:
  (a) amino acids 1–31 of SEQ ID NO: 3;
  (b) amino acids 39–52 of SEQ ID NO: 3;
  (c) amino acids 69–100 of SEQ ID NO: 3; or
  (d) amino acids 127–137 of SEQ ID NO: 3.

3. The antibody of claim 1, wherein the variable region comprises an amino acid sequence set forth as SEQ ID NO: 3.

4. A monoclonal antibody that specifically binds a hepatitis A virus antigen, wherein the antibody comprises a γ1 chain of the variable region encoded by the DNA vector deposited as ATCC Accession number PTA-3839.

5. A nucleic acid molecule encoding the monoclonal antibody of claim 1.

6. The nucleic acid of claim 5, operably linked to a promoter.

7. A vector comprising the nucleic acid of claim 6.

8. The vector of claim 7, further comprising a selectable marker.

9. A host cell comprising the nucleic acid of claim 5.

10. The host cell of claim 9, wherein the host cell is a mammalian host cell.

11. The host cell of claim 10, wherein the host cell is a human host cell.

12. An antigen-binding fragment of the antibody of claim 1.

13. A pharmaceutical composition, comprising the antibody of claim 1 in a pharmaceutically acceptable carrier.

14. A pharmaceutical composition, comprising the antigen binding fragment of claim 12 in a pharmaceutically acceptable earner.

15. A method for detecting hepatitis A virus in a biological sample, comprising
  a) contacting the sample with the antibody of claim 1 to form an immune complex between the antibody and a hepatitis A virus antigen; and
  b) detecting the presence of the immune complex, thereby detecting hepatitis A virus in the biological sample.

16. The method of claim 15, further comprising comparing the binding of the antibody with the binding of a control.

17. The method of claim 15, wherein the biological sample is selected from the group consisting of blood and blood products, liver cells, bone marrow, fecal samples, saliva, sputum, lymphocytes, or other mononuclear cells.

18. A method for detecting hepatitis A virus in a biological sample, comprising
  a) contacting the sample with the antigen binding fragment of claim 12 to form an immune complex between the antibody and a hepatitis A virus antigen; and
  b) detecting the presence of the immune complex thereby detecting hepatitis A virus in a biological sample.

19. The method of claim 18, further comprising comparing the binding of the hepatitis A virus antigen fragment with the binding of a control.

20. The method of claim 18, wherein the biological sample is selected from the group consisting of blood and blood products, liver cells, bone marrow, fecal samples, saliva, sputum, lymphocytes, or other mononuclear cells.

21. A kit for the detection of hepatitis A virus, comprising a container comprising the monoclonal antibody of claim 1.

22. A kit for detecting hepatitis A virus in a biological sample, comprising a container comprising the antibody of claim 1 and instructions for using the kit.

23. A kit for the detection of hepatitis A virus, comprising a container comprising the antigen binding fragment of claim 12.

24. A kit for detecting hepatitis A virus in a biological sample, comprising a container comprising the antigen binding fragment of claim 12 and instructions for using the kit.

* * * * *